(12) United States Patent
Karathanasis et al.

(10) Patent No.: US 12,377,118 B2
(45) Date of Patent: Aug. 5, 2025

(54) NANOPARTICLE CONSTRUCTS FOR SYSTEMIC CO-DELIVERY OF ANTI-TUMOR AGENTS

(71) Applicant: CASE WESTERN RESERVE UNIVERSITY, Cleveland, OH (US)

(72) Inventors: Efstathios Karathanasis, Solon, OH (US); Prabhani Atukorale, Cleveland, OH (US); Wyatt Becicka, Cleveland, OH (US); Peter Bielecki, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 751 days.

(21) Appl. No.: 16/989,473

(22) Filed: Aug. 10, 2020

(65) Prior Publication Data

US 2021/0038633 A1  Feb. 11, 2021

Related U.S. Application Data

(60) Provisional application No. 62/884,963, filed on Aug. 9, 2019.

(51) Int. Cl.
| | | |
|---|---|---|
| *A61K 31/739* | (2006.01) | |
| *A61K 9/127* | (2025.01) | |
| *A61K 31/7016* | (2006.01) | |
| *A61K 31/7084* | (2006.01) | |
| *A61K 47/24* | (2006.01) | |

(52) U.S. Cl.
CPC ............ *A61K 31/739* (2013.01); *A61K 9/127* (2013.01); *A61K 31/7016* (2013.01); *A61K 31/7084* (2013.01); *A61K 47/24* (2013.01)

(58) Field of Classification Search
CPC .. A61K 31/739; A61K 9/127; A61K 31/7016; A61K 31/7084; A61K 47/24; A61K 9/0014; A61K 9/0019; A61K 9/0031; A61K 9/0034; A61K 9/0043; A61K 9/0073; A61K 9/06; A61K 9/08; A61K 9/10; A61K 9/5115; A61K 9/5123; A61K 9/7023

See application file for complete search history.

(56) References Cited

U.S. PATENT DOCUMENTS

| | | | |
|---|---|---|---|
| 2004/0258747 A1* | 12/2004 | Ponzoni | A61K 38/10 |
| | | | 424/93.2 |
| 2005/0032246 A1* | 2/2005 | Brennan | G01N 33/6872 |
| | | | 427/2.11 |
| 2017/0239283 A1* | 8/2017 | Gough | A61K 9/0019 |

FOREIGN PATENT DOCUMENTS

| | | | | |
|---|---|---|---|---|
| CA | 2 318 556 | * | 1/1999 | |
| CA | 2808919 | * | 6/2007 | |
| CA | 3 076 337 | * | 3/2019 | |
| CA | 3088713 | * | 8/2019 | |
| JP | 2014/532071 | * | 12/2014 | |
| KR | 2010/0100875 | * | 9/2010 | |
| WO | 2019/018797 | * | 9/2014 | |
| WO | WO-2014201449 A2 | * | 12/2014 | ............ A61K 35/76 |
| WO | WO-2017027874 A1 | * | 2/2017 | ............ A61K 39/00 |
| WO | WO-2017044803 A1 | * | 3/2017 | ............ A61K 39/39 |
| WO | 2017/091767 | * | 6/2017 | |

\* cited by examiner

*Primary Examiner* — Walter E Webb
(74) *Attorney, Agent, or Firm* — Tarolli, Sundheim, Covell & Tummino LLP

(57) ABSTRACT

An immuno-nanoparticle construct for use in therapeutic applications includes a nanocarrier, a stimulator of interferon (IFN) genes (STING) pathway agonist, and a toll-like receptor 4 (TLR4) agonist, wherein the STING pathway agonist and the TLR4 agonist are co-loaded in the nanoparticle carrier.

27 Claims, 29 Drawing Sheets

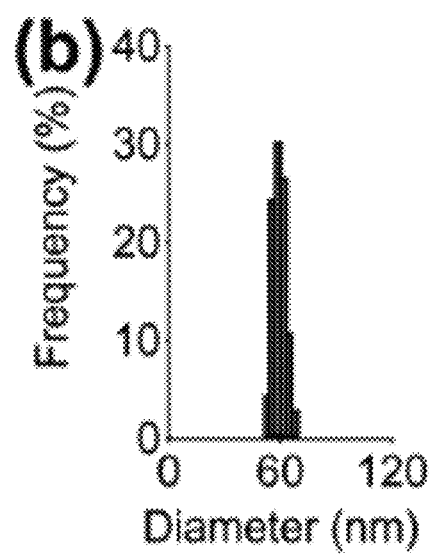
Fig. 3B
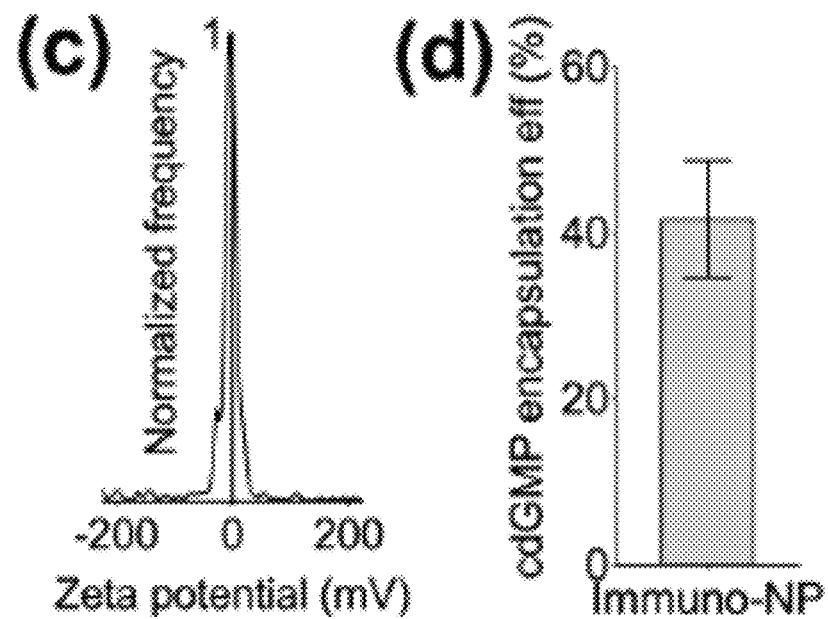
Fig. 3C
Fig. 3D

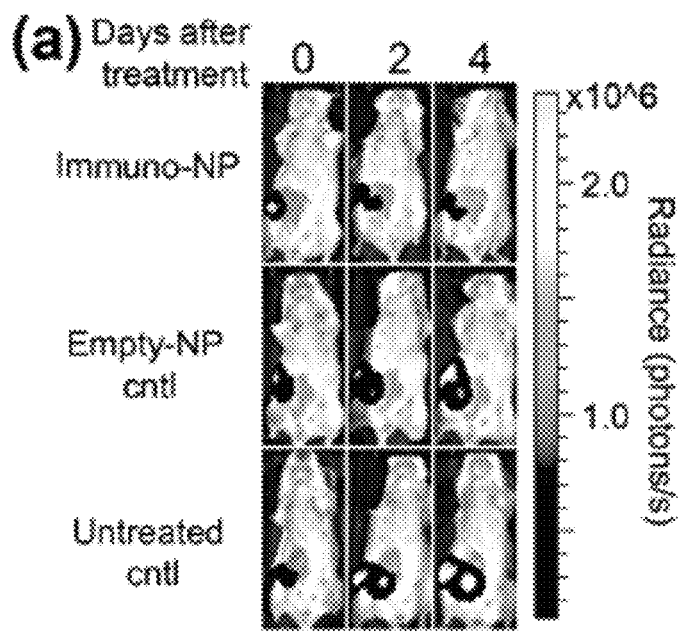
Fig. 5A
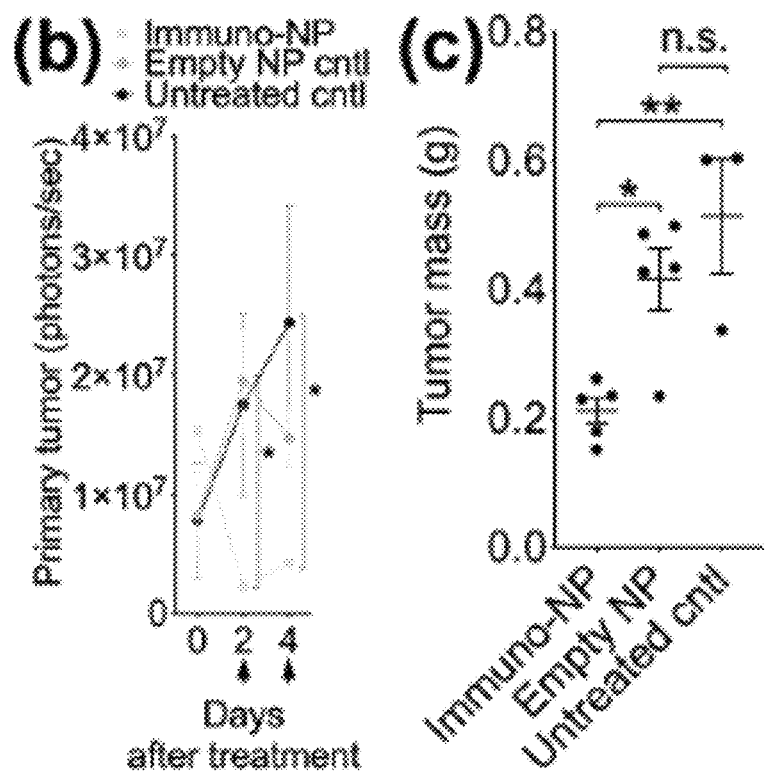
Fig. 5B
Fig. 5C

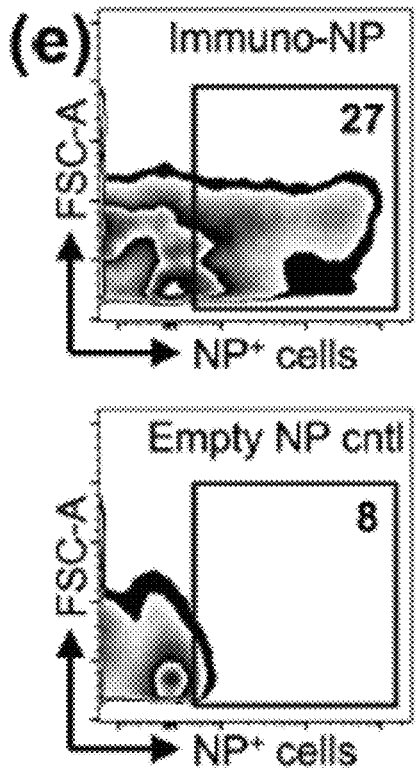
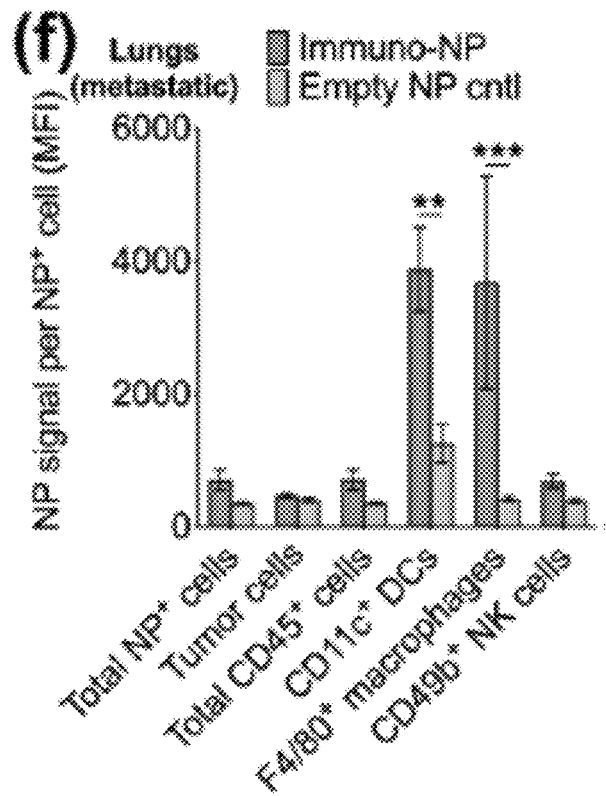
Fig. 6E        Fig. 6F
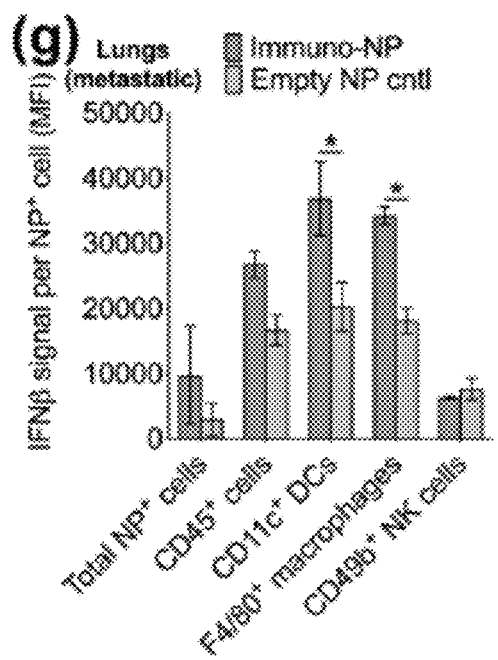
Fig. 6G

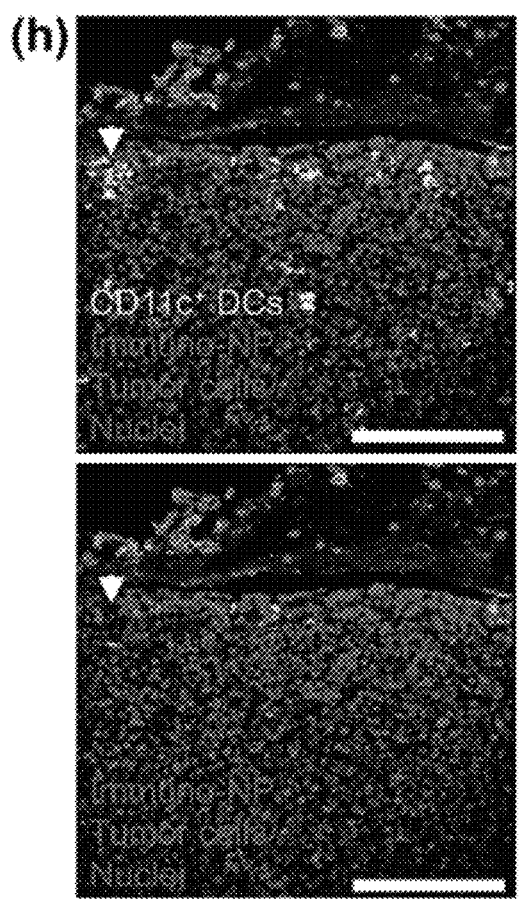
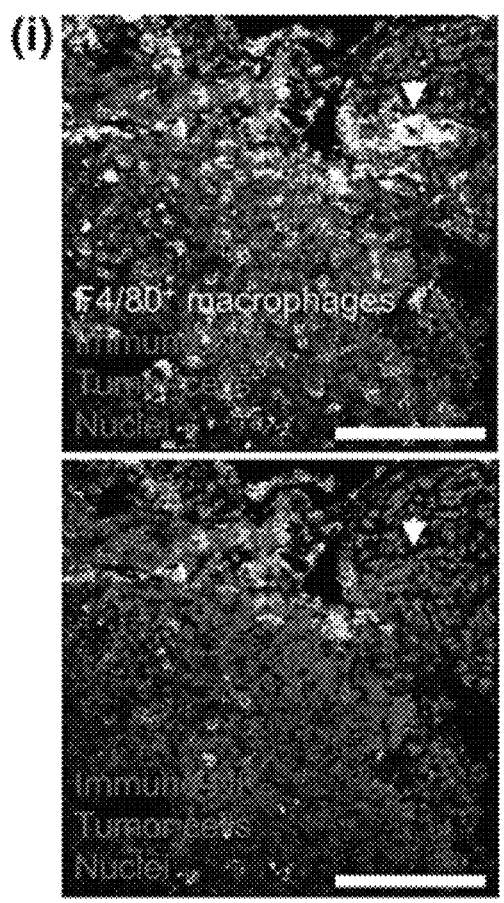
Fig. 6H
Fig. 6I

NANOPARTICLE CONSTRUCTS FOR SYSTEMIC CO-DELIVERY OF ANTI-TUMOR AGENTS

RELATED APPLICATION

This application claims priority from U.S. Provisional Application Nos. 62/884,963 filed Aug. 9, 2019, the subject matter of which are incorporated herein by reference in their entirety.

GOVERNMENT FUNDING

This invention was made with government support under CA177716 and CA198892 awarded by the National Institutes of Health. The government has certain rights in the invention.

TECHNICAL FIELD

This application relates to immuno-nanoparticle constructs for systemic co-delivery of anti-tumor agents to tumor sites and to their use in therapeutic applications.

BACKGROUND

While breast cancer (BC) patients often appear to be within stable remission, ~62% of BC associated deaths occur many years after initial diagnosis highlighting the importance of metastatic dormancy. Disseminated breast cancers escape clinical detection by remaining dormant before reemerging as incurable secondary tumors. In particular, triple-negative BC (TNBC) exhibits a very high risk of metastasis and recurrence. Compared to other subtypes of breast cancer, metastatic relapse will occur in the majority of TNBC patients following treatment. Even though TNBC patients are often responsive to first-line chemotherapy, a small population of dormant disseminated tumor cells (dDTCs) has ceased dividing and are 'potential time bombs' that survive in quiescent/senescent states prior to initiating their explosive metastatic outgrowth. Since dormant disseminated tumor cells are non-proliferative, antimitotic agents, the current standard-of-care, are not effective. Even worse, recurrent TNBCs acquire pro-survival and chemoresistant phenotypes. Further, distant metastatic recurrence of TNBC (mTNBC) tends to occur in visceral organs, including the lungs, liver, and brain. These features make metastatic TNBC nearly incurable.

SUMMARY

Embodiments described herein relate to immuno-nanoparticle constructs for systemic co-delivery of anti-tumor agents to tumor sites and to their use in therapeutic applications. The immuno-nanoparticle constructs include a nanoparticle carrier, a stimulator of interferon (IFN) genes (STING) pathway agonist, and a toll-like receptor 4 (TLR4) agonist. The STING pathway agonist and the TLR4 agonist are co-loaded into the nanoparticle carrier.

In some embodiments, the nanoparticle carrier can include a lipid-based nanoparticle carrier. The lipid-based nanoparticle carrier can be selected from the group consisting of a liposome, a solid lipid nanoparticle (SLN), and a nanostructured lipid carrier (NLC). In certain embodiments, the lipid-based nanoparticle carrier can include a liposome.

In some embodiments, the nanoparticle carrier can include a mesoporous silica nanocore. The mesoporous silica nanocore can be coated with a lipid bilayer. In some embodiments, the TLR4 agonist can be incorporated in the lipid bilayer. In some embodiments, the mesoporous silica nanocore surface is functionalized. In some embodiments, the surface of the mesoporous silica nanocore surface is functionalized with $N^1$-(3-Trimethoxysilylpropyl)diethylenetriamine (TRI-silane).

The TLR4 agonist can include a lipopolysaccharide (LPS) derivative or analog thereof. In some embodiments, the TLR4 agonist can include a lipid A analog, variant, mimetic or derivative. In some embodiments, the TLR4 agonist can include monophosphoryl lipid A (MPLA).

The STING pathway agonist can include a cyclic dinucleotide (CDN). The CDN can be selected from the group consisting of cyclic dimeric guanosine monophosphate (cdGMP), cyclic dimeric adenosine monophosphate (cdAMP), and cyclic GMP-AMP (cGAMP). In certain embodiments, the CDN can include cyclic diguanylate monophosphate (cdGMP).

In some embodiments, the immuno-nanoparticle construct can further include at least one targeting moiety. The at least one targeting moiety can be linked to the exterior surface of the lipid nanoparticle carrier.

Other embodiments relate to a method of treating cancer in a subject. The method can include administering systemically to the subject a therapeutically effective amount of an immuno-nanoparticle construct. The construct includes a nanoparticle carrier, a STING pathway agonist, and a TLR4 agonist. The STING pathway agonist and the TLR4 agonist are co-loaded into the nanoparticle carrier. The STING pathway agonist and the TLR4 agonist synergize to generate a greater amount of Type 1 interferon β in the subject compared to administration of either agent alone.

In some embodiments, the therapeutically effective amount is the amount effective to promote antigen presenting cell (APC) and natural killer (NK) cell driven anti-tumor response in the subject. In some embodiments, the therapeutically effective amount is the amount effective to inhibit tumor microenvironment (TME) immunosuppression in the subject. In some embodiments, the immuno-nanoparticle construct is administered to the subject intravenously.

In some embodiments, the nanoparticle carrier can include a lipid-based nanoparticle carrier. The lipid-based nanoparticle carrier can be selected from the group consisting of a liposome, a solid lipid nanoparticle (SLN), and a nanostructured lipid carrier (NLC). In certain embodiments, the lipid-based nanoparticle carrier can include a liposome.

In some embodiments, the nanoparticle carrier can include a mesoporous silica nanocore. The mesoporous silica nanocore can be coated with a lipid bilayer. In some embodiments, the TLR4 agonist can be incorporated in the lipid bilayer. In some embodiments, the mesoporous silica nanocore surface is functionalized. In some embodiments, the surface of the mesoporous silica nanocore surface is functionalized with $N^1$-(3-Trimethoxysilylpropyl)diethylenetriamine (TRI-silane).

The TLR4 agonist can include a lipopolysaccharide (LPS) derivative or analog thereof. In some embodiments, the TLR4 agonist can include a lipid A analog, variant, mimetic or derivative. In some embodiments, the TLR4 agonist can include monophosphoryl lipid A (MPLA).

The STING pathway agonist can include a cyclic dinucleotide (CDN). The CDN can be selected from the group consisting of cyclic dimeric guanosine monophosphate (cdGMP), cyclic dimeric adenosine monophosphate (cdAMP), and cyclic GMP-AMP (cGAMP). In certain embodiments, the CDN can include cyclic diguanylate monophosphate (cdGMP).

In some embodiments, the immuno-nanoparticle construct can further include at least one targeting moiety. The at least one targeting moiety can be linked to the exterior surface of the lipid nanoparticle carrier.

In some embodiments, the cancer treated is a metastatic cancer. In some embodiments, the cancer treated is selected from breast cancer and melanoma. In some embodiment, the cancer treated is metastatic triple negative breast cancer (mTNBC).

DETAILED DESCRIPTION

Figure 1A:
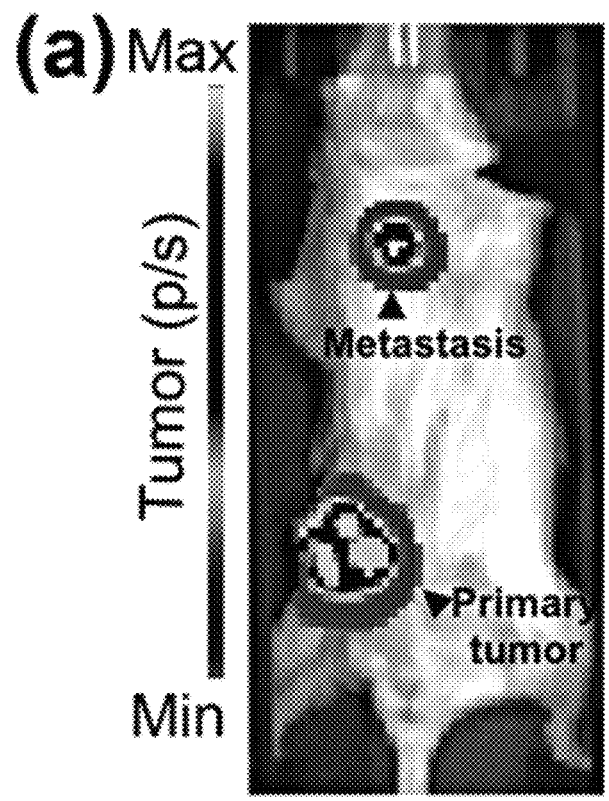
FIGS. 1(A-C) are a schematic of an immuno-nanoparticle (NP)/treatment platform in accordance with one embodiment. (A) Representative image of 4T1 tumor-bearing mouse with both an orthotopic primary tumor mass and lung metastasis (tumor cells express luciferase and luminescence units are photons/s). (B) Schematic of a ~60-nm immuno-NP with surface mPEG and encapsulating both hydrophilic cdGMP within the core and hydrophobic MPLA within the lipid bilayer (red). (C) Schematic of treatment platform where immuno-NPs are delivered systemically to home to tumor sites and collect within the tumor microenvironment (1). Internalization of immuno-NPs (2) results in a tumor site-specific cytokine gradient (3) that in turn leads to APC- and NK cell-driven recruitment and activation of both local and systemic immune cells (4) that mount a robust attack to mediate tumor clearance (5).

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

As used herein, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, aves, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordoma, angiosarcoma, endotheliosarcoma, lymphangiosarcoma, synoviosarcoma and mesothe-liosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

As used herein, the term "polynucleotide" can refer to oligonucleotides, nucleotides, or to a fragment of any of these, to DNA or RNA (e.g., mRNA, rRNA, tRNA) of genomic or synthetic origin, which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids, i.e., oligonucleotides, containing known analogues of natural nucleotides. The term can also encompass nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term can also include peptides and polypeptide fragments, motifs and the like, glycosylated polypeptides, and all "mimetic" and "peptidomimetic" polypeptide forms.

As used herein, the term "small molecule" can refer to lipids, carbohydrates, polynucleotides, polypeptides, or any other organic or inorganic molecules.

As used herein, the terms "treating" or "treatment" of a disease can refer to executing a treatment protocol to eradicate at least one diseased cell. Thus, "treating" or "treatment" does not require complete eradication of diseased cells.

As used herein, the term "targeting moiety" can refer to a molecule or molecules that are able to bind to and complex with a biomarker. The term can also refer to a functional group that serves to target or direct a nanoparticle, therapeutic agent or anti-cancer agent to a particular location, cell type, diseased tissue, or association. In general, a "targeting moiety" can be directed against a biomarker.

As used herein, the term "molecular signature" can refer to a unique expression pattern of one or more biomarkers (e.g., gene(s) or protein(s)) of a cell.

As used herein, the term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

As used herein, the term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 10 amino acids and more typically will comprise at least about 200 amino acids.

As used herein, the term "diabodies" refers to dimeric scFvs. The components of diabodies typically have shorter peptide linkers than most scFvs and they show a preference for associating as dimers.

As used herein, the term "epitope" refers to a physical structure on a molecule that interacts with a selective component. In exemplary embodiments, epitope refers to a desired region on a target molecule that specifically interacts with a selectivity component.

As used herein, the term "Fab'" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

As used herein, the term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

As used herein, the term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

As used herein, the term "immunogen" traditionally refers to compounds that are used to elicit an immune response in an animal and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens".

As used herein, the terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

An "effective amount" can refer to that amount of nanoparticles co-loaded with anti-tumor therapeutic agents, or to the amount of the co-loaded therapeutic agents themselves, that results in amelioration of symptoms or a prolongation of survival in the subject and relieves, to some extent, one or more symptoms of the disease or returns to normal (either partially or completely) one or more physiological or biochemical parameters associated with or causative of the disease. Therapeutic agents can include any agent (e.g., molecule, drug, pharmaceutical composition, etc.) capable of preventing, inhibiting, or arresting the symptoms and/or progression of a disease.

This application relates to immuno-nanoparticle constructs for systemic co-delivery of loaded anti-tumor agents to cancer cells and/or tumor sites and to their use in therapeutic applications. Co-encapsulating anti-tumor agents within nanoparticle carriers to form an immuno-nanoparticle construct can not only prevent toxic dissemination of the loaded therapeutic agents following systemic administration but also allows for their co-delivery to the same target cell. Allowing for systemic administration of the immuno-nanoparticle constructs enables access to the microvasculature and draining to the APC-rich perivasculature regions of the tumor microenvironment (TME) which facilitates intratumoral deposition in both primary tumor sites and sites of metastasis of the immune-potentiating agents, thereby leading to effective APC-driven local and systemic anti-tumor immunity.

Interferon β (IFNβ) drives robust innate immunity, natural killer (NK) cell activity, and APC (dendritic cell and macrophage)-mediated activation of CD8+ T cells and is also pivotal in preventing malignant transformation and de-differentiating cancer stem cells. It was shown that upon target cell internalization of an immuno-nanoparticle construct, the released synergistic immune-potentiating agents co-loaded in a nanoparticle carrier can trigger a robust site-specific cytokine gradient driven largely by IFNβ that results in APC- and NK cell-driven local and systemic immune recruitment (FIG. 1C). It was further shown using a metastatic triple negative breast cancer disease model, that systemic administration of immuno-nanoparticle constructs co-loaded with an agonist of the Stimulator of Interferon Genes (STING) pathway and a Toll-like receptor 4 (TLR4) agonist produced significant anticancer therapeutic outcomes where the co-loaded anti-tumor immune-potentiating agents induced the synergistic production of high levels of Type I IFNβ resulting in extensive upregulation of APCs and NK cells in the blood and tumor sites (see FIG. 4).

The nanoparticle carrier of an immuno-nanoparticle construct described herein may be uniform (e.g., being about the same size) or of variable size. In general, the immuno-nanoparticle constructs can have dimensions small enough to allow the nanoparticle constructs to be systemically administered to a subject and actively or passively targeted to a disease site of the subject (e.g., a tumor microenvironment (TME)). Nanoparticle carriers for use in a construct described herein are ideally nanoparticle carriers capable of protecting cargo from degradation, avoiding non-specific distribution throughout the body that can lead to systemic toxicity and delivering to disease site and facilitate direct uptake by specific cell subpopulations (i.e., APCs) in the tumor microenvironment. In some embodiments, the nanoparticle carrier can have a size that facilitates extravasation of the immuno-nanoparticle construct in cancer therapy allowing the constructs to be taken up by the peripheral APCs or drained from interstitial spaces to the lymphatic lumen and then transported to draining lymph nodes. Typically, the nanoparticle carrier, even when loaded with therapeutic agents, can have a longest straight dimension (e.g., diameter) of about 200 nm or less. In some embodiments, the nanoparticle carrier, can have an average diameter of about 100 nm or less. Smaller nanoparticle carriers, e.g., having average diameters of about 75 nm or less are used in some embodiments. Nanoparticle carriers with diameter of approximately 50-70 nm have been found to be especially efficient at uptake and retention in lymph nodes. In an exemplary embodiment, the nanoparticle carrier, can have an average diameter of about 60 nm.

In some embodiments, the nanoparticle carrier of an immuno-nanoparticle construct can include a lipid-based nanoparticle or polymeric nanoparticle. Lipid-based nanoparticles are a broad and diverse group of nanoparticles that have a high degree of biocompatibility and can encapsulate a wide range of cargos. Lipid-based nanoparticles for use in an immuno-nanoparticle construct described herein can include, but are not limited to, liposomes, solid lipid nanoparticles (SLN) and nanostructured lipid carriers (NLC). Polymeric nanoparticles can include, but are not limited to, poly(beta-amino ester) (PBAE), and pH-responsive polymersomes. Additional nanoparticles for use as a nanocarrier in a construct described herein can include cationic silica nanoparticles (CSiNPs) and lipid coated silica microspheres.

In some embodiments, the nanoparticle carrier is a liposome nanoparticle (see FIG. 1). The main component of liposomes are phospoholipids, which are organized into a bilayer structure due to their amphipathic properties. In the presence of water, they form vesicles improving the solubility and stability of anti-tumor agents once they are loaded into their structure. Liposomes can have positive charges and aqueous cores. The positive charge on liposomes can promote the encapsulation of negatively charged agents and can also facilitate intracellular liposome delivery by electrostatically interactive with negatively charged cell membranes. Liposome nanocarriers can include, but are not limited to, PEG-containing or PEGylated lipids, pH-sensitive cationic lipids, or a soy-PC-DOTAP liposome. In addition to phospholipids, other compounds can be added to liposome formulations, such as cholesterol, to decrease the fluidity of the nanoparticle and increase the permeability of hydrophobic drugs through the bilayer membrane, improving the stability of these nanoparticles in blood. In on example, an immuno-nanoparticle construct can include about 60 nm liposomes prepared from equimolar quantities of DOPC and DPPC and 3 mol % mPEG2000-DSPE.

In some embodiments, the nanoparticle carrier is a SLN or NLC lipid based nanoparticle carrier. SLNs are a colloidal drug delivery system composed of physiological lipids that remain in a solid state at both room and body temperature. The solid lipid used forms a matrix material for drug encapsulation and can include mono-, di- or triglycerides, fatty acids and complex glyceride mixtures. The matrix is typically stabilized by a mixture of surfactants or polymers. NLCs, which were developed from SLNs, can include a mixture of solid and liquid lipids, such as glyceryl tricaprylate, ethyl oleate, isopropyl myristate and glyceryl dioleate.

In other embodiments, the nanoparticle carrier of the immuno-nanoparticle construct can include a mesoporous silica nanocore (MSN). The mesoporous silica protects anti-tumor agents loaded within the nanocore and provides support for surface modification of the MSNs with functional groups. MSNs can be prepared using a base-catalyzed sol-gel process enhanced by the surfactant cetyltrimethylammonium bromide (CTAB) to produce highly ordered mesoporous silica layer. Additionally, various functional groups can be introduced onto the silica surface using well known methods in order to conjugate the nanoparticles with other molecules or substrates.

Use of the term "mesoporous silica" does not preclude materials other than mesoporous silica from also being incorporated within or on the surface of the silica nanocore. In some embodiments, the mesoporous silica nanocore may be substantially spherical with a plurality of pore openings through the surface providing access to the pores. However, the mesoporous silica nanocore can have shapes other than substantially spherical shapes in other embodiments of the current invention. Generally, a layer of mesoporous silica defines an outer surface between the pore openings, as well as side walls within the pores. The pores can extend through a layer of mesoporous silica to another pore opening or can extend only partially through the layer of mesoporous silica such that it has a bottom surface of the pore defined by the layer of mesoporous silica.

The pores of the MSN surface can allow small molecules to diffuse into the outer silica layer of the MSNs. This process, in turn, advantageously allows for highly stable loading of therapeutic anti-tumor immune-potentiating agents with negligible leakage as well as the efficient release of the therapeutic agents from the MSNs from the particle into the cytosol.

The MSN can be coated around the core with a lipid bilayer. In some embodiments, the lipid bilayer can incorporate lipophilic anti-tumor agents and/or be linked to a targeting moiety.

In certain embodiments, the surface of a nanocarrier can be further functionalized to enhance intracellular delivery of the co-loaded agents. For example, the surface of a mesoporous silica nanocore can be functionalized with $N^1$-(3-Trimethoxysilylpropyl)diethylenetriamine to enhance the ability of the nanoparticle construct to escape endosomes, avoid lysosomal degradation and transition to the cytosol to allow for delivery of each agent to its specific intracellular target (e.g., nucleus or ER).

Nanoparticle carriers described herein can be chemically modified to avoid detection by the immune system, and/or to improve the solubility of the therapeutic agents loaded therein. For example, nanoparticle carriers can include a poly(ethylene glycol) (PEG) coating for improved solubility and circulation.

Therapeutic agents co-loaded into and/or incorporated within a nanoparticle carrier to produce an immuno-nanoparticle construct can include two or more anti-tumor immune-potentiating agents capable of inducing Type I interferons in a subject. For example, therapeutic agents for use in a construct described herein may trigger an immune response by targeting target host pattern recognition receptors (PRRs) expressed by cells of the innate immune system, such as dendritic cells, macrophages, monocytes, neutrophils and epithelial cells. In certain embodiments, the therapeutic agents of an immuno-nanoparticle construct are selected from a stimulator of interferon (IFN) genes (STING) agonist and a Toll-like receptor-4 (TLR4) agonist.

In some embodiments, each agent is loaded into a nanocarrier and/or each agent is incorporated within an external layer of the nanoparticle carrier. In other embodiments, a first therapeutic agent is loaded into/encapsulated by a nanocarrier and a second therapeutic agent is incorporated within an external layer of the nanoparticle carrier. In an exemplary embodiment illustrated in FIG. 9A, an immuno-nanoparticle construct includes an MSN nanoparticle carrier loaded with/encapsulating a STING agonist, wherein the MSN is coated with an external lipid bilayer that incorporates a TLR4 agonist.

In some embodiments, a therapeutic agent of an immuno-nanoparticle construct can include a STING agonist. The activation of STING, an intracellular receptor residing in the endoplasmic reticulum, can enhance antitumor immunity through the induction of a variety of pro-inflammatory cytokines and chemokines, including type I IFNs. Several natural and synthetic STING agonists have been discovered or developed for use in immunotherapy. Upon binding to CDNs, STING translocates from the ER to the Golgi apparatus and further to the perinuclear microsomes or punctuate structures, which in turn recruit the downstream TANK-binding kinase 1 (TBK1) and the transcription factor interferon regulatory factor 3 (IRF3), leading to induction of type I IFNs.

In some embodiments, a STING agonist for use in compositions and methods described here can include cyclic dinucleotides (CDNs), such as cyclic dimeric guanosine monophosphate (c-di-GMP or cdGMP), cyclic dimeric adenosine monophosphate (c-di-AMP or cdAMP), and cyclic GMP-AMP (cGAMP, such as 3'3'-cGAMP and 2'3'cGAMP). In some embodiments, CDNs can be chemically modified to improve biostability. An exemplary chemically modified CDN is ADU-S1000, also known as ML RR-S2 CDA.

In another embodiment, a STING activating agent can include a small molecule amidobenzimidazole (ABZI) compound. In some embodiments, a STING activating agent can include two symmetry-related ABZI-based compounds linked to form a diABZI compound, in order to enhance both binding to STING and cellular function.

In some embodiments, a therapeutic agent of an immuno-nanoparticle construct can include a TLR4 agonist. TLR4 is expressed by cells of the innate immune system, including conventional dendritic cells and macrophages. Triggering via TLR4 induces a signaling cascade that utilizes both the MyD88- and TRIF-dependent pathways, leading to NF-1B and IRF3/7 activation, respectively.

Various useful TLR4 agonists are known in the art, many of which are analogs or derivatives of endotoxin or lipopolysaccharide (LPS). For example, LPS-derivatives for use as a TLR4 agonist can be made synthetically to provide more control over the structure of the most potent aspect of the LPS, lipid A. Therefore, in some embodiments, the LPS-derivative can include a synthetic lipid A variant, derivative, mimetic or analog.

The TLR4 agonist monophosphoryl lipid A (MPLA) has been shown to trigger a strong pro-inflammatory Th1 cytokine response. Thus, in some embodiments, TLR4 agonists can include MPLA, a derivative or analog thereof. MPLA can include either synthetic or naturally derived MPLA. In some embodiments, the TLR4 agonist can include 3d-MPL (i.e. 3-O-deacylated monophosphoryl lipid A; also known as 3-de-O-acylated monophosphoryl lipid A or 3-O-desacyl-4'-monophosphoryl lipid A). This derivative of the monophosphoryl lipid A portion of endotoxin has a de-acylated position 3 of the reducing end of glucosamine. 3d-MPL can be prepared from a heptoseless mutant of *Salmonella minnesota* and is chemically similar to lipid A but lacks an acid-labile phosphoryl group and a base-labile acyl group.

In some embodiments, TLR4 agonists can include aminoalkyl glucosaminide phosphate compounds (AGPs). AGPs are a monosaccharide mimetic of the lipid A protein of bacterial LPS and have been developed with ether and ester linkages on the acyl chains of the compound. Processes for making these compounds are known and disclosed, for example, in WO 2006/016997, U.S. Pat. Nos. 7,288,640 and 6,113,918, and WO 01/90129. Exemplary AGPs for use in a composition described herein can include, but are not limited to, RC-529, CRX-524, CRX-527 CRX-547, CRX-601 and CRX-602. Additional lipid A analogs for use in an immuno-nanoparticle construct described herein can include the water-soluble tri-acyl lipid A, OM-174. TLR4 agonist can also include the synthetic glucopyranosyl lipid A (GLA), a stable emulsion of GLA, or its ammonium salt.

In some embodiments, the immuno-nanoparticle constructs can additionally or optionally include at least one targeting moiety that is capable of targeting and/or adhering the nanoparticle construct to a cell or tissue of interest. The targeting moiety can comprise any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. Other examples of biomarkers that the targeting moiety can interact with include molecules associated with a particular disease. For example, the biomarkers can include cell surface receptors implicated in cancer development, such as epidermal growth factor receptor and transferrin receptor, or cancer metastasis, such as $\alpha_v\beta_3$ integrin. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting moieties can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can include an antibody, such as a monoclonal antibody, a polyclonal antibody, or a humanized antibody. The antibody can include Fv fragments, single chain Fv (scFv) fragments, Fab' fragments, F(ab')$_2$ fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized and boosted one or more times with the desired immunogen(s), antibody-producing hybridomas may be prepared and screened according to well-known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate a targeting moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

The targeting moiety need not originate from a biological source. The targeting moiety may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moieties may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, a targeting moiety as described herein may comprise a homing peptide, which selectively directs the nanoparticle to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460;

Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,6999; 6,068,829; 6,174,687; 6,180,084; 6,232, 287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon-based mutagenesis method, which can be used to produce random peptides or randomly or desirably biased peptides (see, e.g., U.S. Pat. No. 5,264, 563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In still other embodiments, the targeting moiety may comprise a ligand molecule, including, for example, ligands which naturally recognize a specific desired receptor of a target cell, such as a Transferrin (Tf) ligand. Such ligand molecules include ligands that have been modified to increase their specificity of interaction with a target receptor, ligands that have been modified to interact with a desired receptor not naturally recognized by the ligand, and fragments of such ligands.

In other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated which mimic those residues which facilitate the interaction. Such mimetics may then be used as a targeting moiety to deliver the composition to a target cell. For instance, non-hydrolyzable peptide analogs of such resides can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

The targeting moiety may be attached directly to the immuno-nanoparticle construct. In one embodiment, a targeting moiety may be conjugated onto an amine-functionalized mesoporous silica nanocore nanoparticle via maleimide chemistry. In some embodiments, the targeting moiety may be associated with or coupled to the nanoparticles using a linker. The linker can be of any suitable length and contain any suitable number of atoms and/or subunits. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

In some embodiments, the immuno-nanoparticle constructs can include multiple types of targeting moieties and the spacing and location of the targeting moieties on each nanoparticle construct can be controlled to facilitate delivery, targeting, and/or therapeutic efficacy of the co-loaded therapeutic cargo.

The immuno-nanoparticle constructs described herein can be used in therapeutic applications to deliver a cargo of two or more anti-tumor immune-potentiating therapeutic agents to cancer cells and/or tumor tissue of a subject upon systemic administration (e.g., intravenous, intravascular, intraarterial infusion) to the subject. It is believed that systemically administered immuno-nanoparticle constructs described herein can reach and preferably accumulate at a site of cancer by extravasation through leaky tumor endothelium in tumor interstitium.

Therefore, in another aspect, the present invention provides a method of treating cancer in a subject, by systemically administering to a subject in need thereof a therapeutically effective amount of an immuno-nanoparticle construct, the construct including a nanoparticle carrier, a STING pathway agonist, and a TLR4 agonist, wherein the STING pathway agonist and the TLR4 agonist are encapsulated in the nanoparticle carrier.

When used to treat cancer, the immuno-nanoparticle constructs can be administered to a subject who has been diagnosed with cancer, in order to stimulate or increase an interferon β-driven anti-tumor immune response against the subject's cancer cells. As is known to those skilled in the art, there are a variety of methods of identifying (i.e., diagnosing) a subject who has cancer. For example, diagnosis of cancer can include one or more of a physical exam, laboratory tests, imaging analysis, and biopsy. After cancer is diagnosed, a variety of tests may be carried out to look for specific features characteristic of different types and or the extent of cancer in the subject. These tests include, but are not limited to, bone scans, X-rays, immunophenotyping, flow cytometry, and fluorescence in situ hybridization testing. For example, typical methods of diagnosing triple-negative breast cancer can include, but are not limited to, a physical exam, digital mammogram, breast MRI, breast ultrasound, stereotactic core and/or open tumor biopsy, as well as lab tests to determine if the tumor tissue expresses estrogen, progesterone, and HER-2/neu or not.

Alternately, the immuno-nanoparticle constructs composition can be administered to a subject who has not been diagnosed with cancer as a means of preventing or decreasing the risk or likelihood of cancer development. In some embodiments, the subject being treated using compositions described herein has been characterized as being a subject having a high or increased risk of developing cancer. Subjects can be characterized as being at high or increased risk of developing cancer as a result of, for example, family history, genetic testing, or high exposure to cancer-causing environmental conditions.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

The cancers treated by a method described herein can include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, glioblastoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, fallopian tube cancer, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In certain embodiments, cancers treated in accordance with a method described herein include breast cancers and melanoma. In some embodiments, the breast cancer is triple negative breast cancer. In some embodiments, the cancer is a malignant melanoma.

In some embodiments, a method of treating cancer described herein can include administering an additional therapeutic or cancer therapy to the subject. A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy.

In some embodiments, the method can include the step of administering a therapeutically effective amount of an additional anticancer therapeutic agent to the subject. Additional anticancer therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA. In some embodiments, cytotoxic compounds are included in an anticancer agent described herein. Cytotoxic compounds include small-molecule drugs such as doxorubicin, methotrexate, vincristine, and pyrimidine and purine analogs, referred to herein as antitumor agents. In particular embodiments, an additional anticancer therapeutic agent can include a corticosteroid such as but not limited to prednisone.

The additional anticancer therapeutic agent can include an anticancer or an antiproliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of anticancer therapeutic agents that can be administered in combination with an immuno-nanoparticle construct described herein include Taxol, Adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a;

interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; temozolomide, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In certain embodiments, additional therapeutic agents administered to a subject for the treatment of triple negative breast cancer as described herein can include one or more of an anthracycline, such as adriamycin, an alkylating agent such as Cytoxan (cyclophosphamide), an antimetabolite such as Fluorouracil (5FU), and a taxane, such as Taxol or Taxotere. In other embodiments, additional therapeutic agents administered to a subject for the treatment of melanoma as described herein can include one or more of Aldesleukin, Binimetinib, Braftovi (Encorafenib), Cobimetinib, Cotellic (Cobimetinib), Dabrafenib Mesylate, Dacarbazine, Encorafenib, Imlygic (Talimogene Laherparepvec), Intron A (Recombinant Interferon Alfa-2b), Keytruda (Pembrolizumab), Mekinist (Trametinib), Mektovi (Binimetinib), Nivolumab, Opdivo (Nivolumab), Peginterferon Alfa-2b, PEG-Intron (Peginterferon Alfa-2b), Recombinant Interferon Alfa-2b, Sylatron (Peginterferon Alfa-2b), Tafinlar (Dabrafenib Mesylate), Talimogene Laherparepvec, Trametinib, Vemurafenib, Yervoy (Ipilimumab), and Zelboraf (Vemurafenib).

In some embodiments, the anti-cancer therapy administered to the subject in addition to the immuno-nanoparticle constructs can include the cancer ablation therapy. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins. Another method of ablating cancer such as breast cancer that has been treated with an anti-cancer particle composition of the present invention is to conducting surgery to remove the cancer tissue (e.g., breast cancer tissue) from the subject. Types of surgery for breast cancer vary depending on the nature of the breast cancer, and include lumpectomy, partial or segmental mastectomy or quadrantectomy, simple or total mastectomy, radical mastectomy, and modified radical mastectomy. Appropriate surgeries for treating other types of cancer are known to those skilled in the art.

In some embodiments, ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers). In contrast, specific cancer immunotherapy is based on certain antigens that are preferentially or solely expressed on cancer cells or predominantly expressed by other cells in the context of malignant disease (usually in vicinity of the tumor site). Specific cancer immunotherapy can be grouped into passive and active approaches.

In passive specific cancer immunotherapy substances with specificity for certain structures related to cancer that are derived from components of the immune system are administered to the patient. The most prominent and successful approaches are treatments with humanized or mouse/human chimeric monoclonal antibodies against defined cancer associated structures (such as Trastuzumab, Rituximab, Cetuximab, Bevacizumab, Alemtuzumab). The pharmacologically active substance exerts is activity as long as a sufficient concentration is present in the body of the patient, therefore administrations have to be repeated based on pharmacokinetic and pharmacodynamic considerations.

On the other hand, active specific cancer immunotherapy aims at antigen-specific stimulation of the patient's immune system to recognize and destroy cancer cells. Active specific cancer immunotherapy therefore, in general, is a therapeutic vaccination approach. There are many types of cancer vaccine approaches being pursued, such as vaccination with autologous or allogeneic whole tumor cells (in most cases genetically modified for better immune recognition), tumor cell lysates, whole tumor associated antigens (produced by means of genetic engineering or by chemical synthesis), peptides derived from protein antigens, DNA vaccines encoding for tumor associated antigens, surrogates of tumor antigens such as anti-idiotypic antibodies used as vaccine antigens, and the like. These manifold approaches are usually administered together with appropriate vaccine adjuvants and other immunomodulators in order to elicit a quantitatively and qualitatively sufficient immune response (many novel vaccine adjuvant approaches are being pursued in parallel with the development of cancer vaccines). Another set of cancer vaccine approaches rely on manipulating dendritic cells (DC) as the most important antigen presenting cell of the immune system. For example, loading with tumor antigens or tumor cell lysates, transfection with genes encoding for tumor antigens and in-vivo targeting are suitable immunotherapies that can be used together with the virus or virus-like particles of the invention for cancer treatment.

In some embodiments, ablating the cancer includes administering a therapeutically effective amount of radiotherapy (RT) to the subject. In some embodiments, RT is administered prior to administration of the immuno-nanoparticle construct.

Radiotherapy uses high-energy rays to treat disease, usually x-rays and similar rays (such as electrons). Radiotherapy administered to a subject can include both external and internal. External radiotherapy (or external beam radiation) aims high-energy x-rays at the tumor site including in some cases the peri-tumor margin. External radiotherapy typically includes the use of a linear accelerator (e.g., a Varian 2100C linear accelerator). External radiation therapy can include three-dimensional conformal radiation therapy (3D-CRT), image guided radiation therapy (IGRT), intensity modulated radiation therapy (IMRT), helical-tomotherapy, photon beam radiation therapy, proton beam radiation therapy, stereotactic radiosurgery and/or sterotactic body radiation therapy (SBRT).

Internal radiotherapy (brachytherapy) involves having radioactive material placed inside the body and allows a higher dose of radiation in a smaller area than might be possible with external radiation treatment. It uses a radiation source that is usually sealed in an implant. Exemplary implants include pellets, seeds, ribbons, wires, needles, capsules, balloons, or tubes. Implants are placed in your body, very close to or inside the tumor. Internal radiotherapy can include intracavitary or interstitial radiation. During intracavitary radiation, the radioactive source is placed in a body cavity (space), such as the uterus. With interstitial radiation, the implants are placed in or near the tumor, but not in a body cavity.

In some embodiments, an immune checkpoint inhibitor can be further administered to eradicate suppressive regulatory T cells prior to RT. Exemplary checkpoint inhibitors can include CTLA4, 4-1BB and PD-1/PDL-1 inhibitors. The cytotoxic T-lymphocyte-associated antigen 4 (CTLA-4) and programmed death 1 (PD-1) immune checkpoints are negative regulators of T-cell immune function and inhibition of these targets, results in increased activation of the immune system. Therefore, in some embodiments, a checkpoint inhibitor administered to a subject can include a CTLA-4, 4-1BB and/or PD-1 inhibitor.

For example, Ipilimumab, an inhibitor of CTLA-4, is approved for the treatment of advanced or unresectable melanoma. Nivolumab and pembrolizumab, both PD-1 inhibitors, are approved to treat patients with advanced or metastatic melanoma and patients with metastatic, refractory non-small cell lung cancer. In addition, the combination of ipilimumab and nivolumab has been approved in patients with BRAF WT metastatic or unresectable melanoma. In some embodiments, an immune checkpoint agonistic agent, such as an OX40 agonistic agent, can be further administered can be administered promote immune activation of cytotoxic T-cells. In another example, immuno-nanoparticle constructs described herein can be administered in combination with a PD-L1 inhibitor and an OX40 agonist.

When used in vivo, the immuno-nanoparticle constructs and/or additional anti-cancer therapeutic agents described herein can be administered as a pharmaceutical composition, comprising a mixture, and a pharmaceutically acceptable carrier. The anti-cancer virus particles may be present in a pharmaceutical composition in an amount from 0.001 to 99.9 wt %, more preferably from about 0.01 to 99 wt %, and even more preferably from 0.1 to 95 wt %.

The immuno-nanoparticle constructs, or pharmaceutical compositions comprising these constructs, may be administered by any method designed to provide the desired effect. Administration may occur enterally or parenterally; for example orally, topically, rectally, intracisternally, intravaginally, intraperitoneally or locally. Parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device. In some embodiment, the immuno-nanoparticle constructs may be administered topically. Anti-cancer particles can be topically administered passively for example, by direct application of an ointment or a skin patch, or administered actively, for example, using a nasal spray or inhalant, in which case one component of the composition is an appropriate propellant or through the use of facilitated absorption through the skin using, for example, transdermal iontophoresis.

For parenteral administration, constructs of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The pharmaceutical compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

Suitable pharmaceutically acceptable carriers may contain inert ingredients which do not unduly inhibit the biological activity of the compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

A pharmaceutically acceptable carrier for a pharmaceutical composition can also include delivery systems known to the art for entraining or encapsulating drugs, such as anticancer drugs. In some embodiments, the disclosed compounds can be employed with such delivery systems including, for example, liposomes, nanoparticles, nanospheres, nanodiscs, dendrimers, and the like. See, for example Farokhzad, O. C., Jon, S., Khademhosseini, A., Tran, T. N., Lavan, D. A., and Langer, R. (2004). "Nanoparticle-aptamer bioconjugates: a new approach for targeting prostate cancer cells." Cancer Res., 64, 7668-72; Dass, C. R. (2002). "Vehicles for oligonucleotide delivery to tumours." J.

Pharm. Pharmacol., 54, 3-27; Lysik, M. A., and Wu-Pong, S. (2003). "Innovations in oligonucleotide drug delivery." J. Pharm. Sci., 92, 1559-73; Shoji, Y., and Nakashima, H. (2004). "Current status of delivery systems to improve target efficacy of oligonucleotides." Curr. Pharm. Des., 10, 785-96; Allen, T. M., and Cullis, P. R. (2004). "Drug delivery systems: entering the mainstream." Science, 303, 1818-22. The entire teachings of each reference cited in this paragraph are incorporated herein by reference.

Suitable doses can vary widely depending on the therapeutic being used. A typical pharmaceutical composition for intravenous administration would be about 0.1 mg to about 10 g per subject per day. However, in other embodiments, doses from about 1 mg to about 1 g, or from about 10 mg to about 1 g can be used. Single or multiple administrations of the compositions may be administered depending on the dosage and frequency as required and tolerated by the subject. In any event, the administration regime should provide a sufficient quantity of the composition of this invention to effectively treat the subject.

Useful dosages of the additional anticancer agents, such as antimitotic agents, and immuno-nanoparticle constructs can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the additional anticancer agents and/or immuno-nanoparticle constructs vary depending upon many different factors, including means of administration, target site, physiological state of the patient, whether the patient is human or an animal, other medications administered, and whether treatment is prophylactic or therapeutic. The skilled artisan will be able to determine appropriate dosages depending on these and other factors using standard clinical techniques.

In some embodiments, the therapeutically effective amount of an immuno-nanoparticle construct described herein is the amount effective to promote antigen presenting cell (APC) and natural killer (NK) cell driven anti-tumor response in the subject. In some embodiments, the therapeutically effective amount of an immuno-nanoparticle construct described herein is the amount effective to inhibit tumor microenvironment (TME) immunosuppression in the subject.

Formulations including immuno-nanoparticle constructs for administration to a subject in need thereof described herein may be conveniently presented in unit dosage form and may be prepared by any of the methods well known in the art of pharmacy. Preferably, such methods include the step of bringing the immuno-nanoparticle constructs into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect.

One skilled in the art can readily determine an effective amount of immuno-nanoparticle constructs and/or additional cancer therapeutics to be administered to a given subject, by taking into account factors such as the size and weight of the subject; the extent of disease penetration; the age, health and sex of the subject; the route of administration; and whether the administration is local or systemic. Those skilled in the art may derive appropriate dosages and schedules of administration to suit the specific circumstances and needs of the subject. For example, suitable doses of the immuno-nanoparticle constructs to be administered can be estimated from the volume of cancer cells to be killed or volume of tumor to which the constructs are being administered.

The methods described herein contemplate single as well as multiple administrations, given either simultaneously or over an extended period of time. A pharmaceutically acceptable composition containing the immuno-nanoparticle constructs and/or additional cancer therapeutic can be administered at regular intervals, depending on the nature and extent of the cancer's effects, and on an ongoing basis. Administration at a "regular interval," as used herein, indicates that the therapeutically effective amount is administered periodically (as distinguished from a one-time dose). In one embodiment, the pharmaceutically acceptable composition containing the immuno-nanoparticle construct and/or an additional cancer therapeutic is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased.

For example, the administration of immuno-nanoparticle constructs and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

In some embodiments, the immuno-nanoparticle constructs administered to a subject can be formulated in a slow release formulation in order to sustain immune stimulation by maintaining a therapeutic concentration of the immuno-nanoparticle constructs, (e.g., at the site of a tumor) while alleviating the need for frequent administrations. In some embodiments, a slow release formulation can include a polymer-based hydrogel or a dendrimer.

The following examples are for the purpose of illustration only and are not intended to limit the scope of the claims, which are appended hereto.

Example 1

Nanoparticle Encapsulation of Synergistic Immune Agonists Enables Systemic Co-Delivery to Tumor Sites and Interferon β-Driven Anti-Tumor Immunity In this example we describe an immuno-nanoparticle construct co-loaded with cyclic diguanylate monophosphate (cdGMP), an agonist of the Stimulator of Interferon Genes (STING) pathway, and monophosphoryl lipid A (MPLA), a Toll-like receptor 4 (TLR4) agonist, which synergize to produce high levels of immune-potentiating Type I interferon and by delivering the co-loaded agents to the same target cell. Using a murine model of metastatic triple-negative breast cancer, systemic delivery of these immuno-nanoparticles resulted in significant therapeutic outcomes due to extensive upregulation of APCs and natural killer (NK) cells in the blood and tumor compared to control treatments. These results indicate that nanoparticles can facilitate systemic delivery of multiple immune-potentiating cargoes for effective APC-driven local and systemic anti-tumor immunity.

Here we present a nanotechnology approach to promote tumor site-specific immunity by co-encapsulating two synergistic immune-potentiating agents within a single liposomal nanoparticle that is delivered systemically to accumulate preferentially within the APC-rich perivascular areas of the tumor and drive an IFNβ-mediated anti-tumor immune response. Co-encapsulation within a nanoparticle not only prevents toxic systemic dissemination of these therapeutics, but also guarantees their co-delivery to the same target cell. We selected the 4T1 murine model of triple-negative breast cancer (TNBC) as an optimal test-bed for this therapy since it is poorly immunogenic with spontaneous metastasis and profound immunosuppression, as is reminiscent of clinical TNBC. A total of 12-17% of newly diagnosed early breast cancers are TNBCs, which form the most aggressive subset of breast cancer with a very high risk of recurrence and metastasis, leading to disproportionate mortality. Our strategy to drive local tumor site-specific immunity can have significant impact on treatment, which is otherwise severely limited.

We hypothesized that harnessing multiple overlapping innate immune pathways could trigger a more potent, synergistic cytokine response. We elected to co-deliver two strong inducers of Type I interferons: the STING agonist cyclic diguanylate monophosphate (cdGMP) and the Toll-like receptor 4 (TLR4) agonist monophosphoryl lipid A (MPLA), which was clinically approved for use as the first molecular vaccine adjuvant in humans. Both cdGMP and MPLA target host pattern recognition receptors (PRRs), which recognize conserved, immunogenic molecules from viruses and bacteria (i.e., specific nucleic acids, cell membrane components) to trigger the appropriate immune response.

Figure 1B:
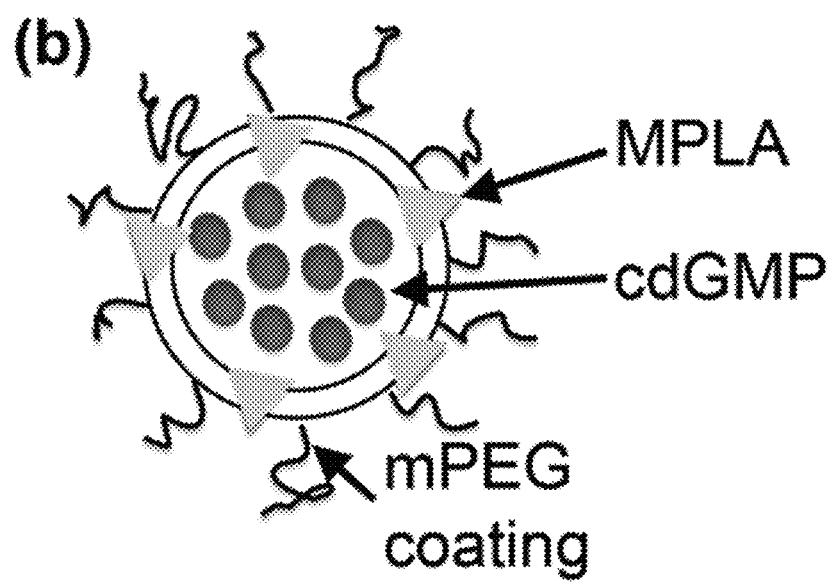
Figure 1C:
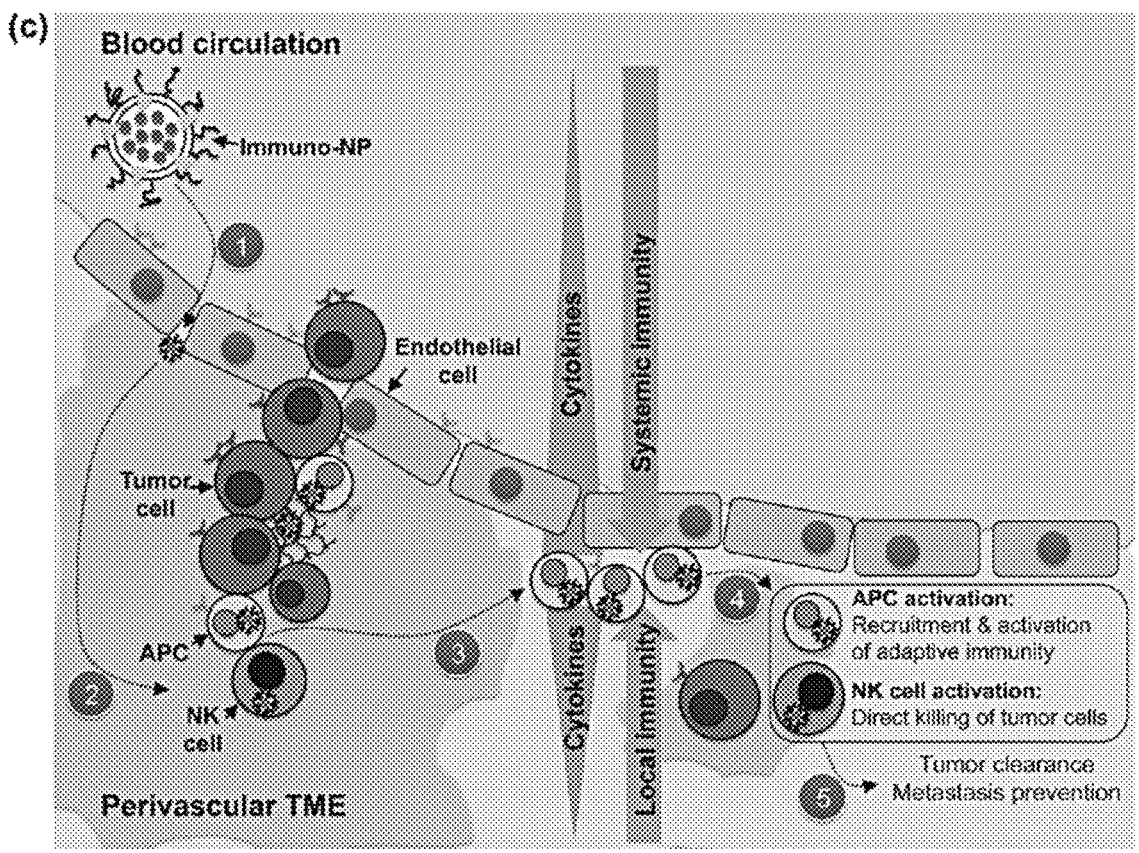

Here we exploited the leaky endothelium of advanced TNBC tumors to achieve efficient draining of systemically delivered about 60-nm cdGMP/MPLA-encapsulated immuno-nanoparticles (immuno-NPs, FIG. 1). For our primary investigations, we selected the 4T1 murine model of metastatic TNBC as a clinically relevant test model, where orthotopic inoculation of cells in the mammary fat pad has been shown to lead to metastasis predominantly in the lungs and lymph nodes (FIG. 1A). To illustrate the broad application of immuno-NPs, we selected an all-purpose, versatile liposome and co-encapsulated both hydrophilic cdGMP (within the core) and hydrophobic MPLA (within the lipid bilayer) on the same nanoparticle (FIG. 1B). We elected to use relatively smaller liposomes in the 60-nm size range because of their established benefits in draining to and retention within tumors and we incorporated a poly(ethylene glycol) (PEG) coating for improved solubility and circulation. The systemic administration of our immuno-NPs resulted in significant intratumoral deposition in both the primary tumor and sites of metastasis, predominantly in APC-rich perivascular regions of the TME. Upon internalization of the nanoparticles, released cdGMP and MPLA triggered a robust, synergistic site-specific cytokine gradient driven largely by IFNβ that resulted in APC- and NK cell-driven local and systemic immune recruitment (FIG. 1C).

Materials and Methods

Nanoparticle Synthesis & Characterization

To synthesize nanoparticles, lipid films were prepared consisting of 48.5 mol % DOPC (1,2-dioleoyl-sn-glycero-3-phosphocholine, Avanti), 48.5 mol % DPPC (1,2-dipalmitoyl-sn-glycero-3-phosphocholine, Avanti, Alabaster, AL), and 3 mol % mPEG2000-DSPE (methoxy-poly(ethylene glycol)-2000 1,2-distearoyl-sn-glycero-3-phosphoethanolamine-N, Laysan Bio, Arab, AL). MPLA (100 µg per 42 µmol lipid) was added prior to film formation (Sigma-Aldrich, St. Louis, MO). Lipid films were hydrated in phosphate-buffered saline (PBS) containing 200 µg cyclic di-GMP (InvivoGen, San Diego, CA), heated to 60° C. for 1 hr, and vortexed for 30 sec every 10 min. Samples were ultra-sonicated on ice for 5 min at alternating power settings (7 W and 5 W every 30 sec). Nanoparticles were dialyzed in PBS for 2-4 hr and stored at 4° C. Size and surface charge were measured via DLS and zeta potential measurements, respectively (Beckman Coulter, Brea, CA). Encapsulated cyclic di-GMP was measured using size exclusion HPLC (high permeation liquid chromatography, Shimadzu, Kyoto, Japan). Stability studies were conducted at 25° C. and 37° C. For immuno-NP fluorescence studies, NPs were synthesized by incorporating 0.2 mol % of DiI, DiD, or DiR purchased from Thermo Fisher Scientific (Waltham, MA).

Cell Lines and Animal Models

Murine B16F10 melanoma cells and RAW 264.7 macrophages (ATCC, Manassas, VA) were cultured in DMEM medium (Gibco, Gaithersburg, MD) containing 10% fetal bovine serum (FBS, HyClone, Logan, UT). Murine 4T1 triple-negative breast cancer cells expressing green fluorescent protein (GFP) and luciferase were cultured in RPMI medium (Gibco, Gaithersburg, MD) containing 10% FBS. STR authentication was used for cell line authenticity. Cell lines were routinely tested and confirmed to be free of Mycoplasma contamination.

For 4T1 studies, BALB/c mice (Jackson Laboratories, Bar Harbor, ME) were inoculated by orthotopic injection of $5 \times 10^5$ 4T1 cells in mammary fat pad #9. Tumors were monitored by bioluminescence imaging (BLI, IVIS Spectrum, Perkin Elmer, Waltham, MA) and caliper measurements. Tumor-bearing animals were treated on day 10 after inoculation. Nanoparticles and free immuno-agents were administered by intravenous (i.v.) or intratumoral (i.t.) injection as noted. Anti-PD-1 (250 µg, clone RMP1-14) and anti-CTLA-4 (100 µg, clone 9D9) (BioXCell, West Lebanon, NH) were administered by intraperitoneal (i.p.) injection. For ALT/AST measurements of hepatotoxicity, mice were bled retro-orbitally and serum was analyzed by the University Hospitals Pathology Core (Cleveland, OH).

For B16F10 studies, C57/BL6 mice (Jackson Laboratories, Bar Harbor, ME) were inoculated by orthotopic subcutaneous (s.c.) injection of $1 \times 10^6$ B16F10 cells on the dorsal flank. Tumors were monitored by caliper measurements. Tumor-bearing animals were treated on day 7 after inoculation. Nanoparticles were administered by i.v. injection.

Spectrum Fluorescence Imaging

For Spectrum studies, fluorescent nanoparticles were prepared with 0.2 mol % DiD (Invitrogen, Carlsbad, CA). 4T1 tumor-bearing mice were injected with fluorescent nanoparticles and either live-animal imaging or imaging of whole excised organs was performed using an IVIS Spectrum. Quantitative biodistribution of nanoparticles in the blood plasma was calculated using a value of 77 mL/kg for average total blood volume of a mouse (Jackson Laboratories, Bar Harbor, ME).

Fluorescence Molecular Tomography

For fluorescence molecular tomography (FMT) studies, fluorescent nanoparticles were prepared with 1 mol % DSPE-VivoTag-800 (Perkin Elmer, Waltham, MA). 4T1 tumor-bearing mice were injected with fluorescent nanoparticles, euthanized at noted time points, and FMT (Perkin Elmer, Waltham, MA) was used to image whole excised organs Flow Cytometry Anti-mouse CD45 (30-F11), Ly-6G (1A8), Ly-6C (AL-21), CD11b (M1/70), CD11c (HL3), F4/80 (BM8), CD49b (DX5), CD3F (145-2C11), CD4 (GK1.5), CD8a (Ly-2, 53-6.7), and CD19 (1D3) flow cytometry antibodies were purchased from BD Biosciences (San Jose, CA). Flow cytometry analysis was performed 48 hr after treatment. Blood samples were obtained via retro-orbital bleeding and mice were euthanized immediately afterwards and tumors and spleens were harvested. Organs were gently disrupted into single-cell suspensions in progressive steps. Cells were stained to identify immune cell populations with a blocking step using anti-mouse CD18/CD32 and analyzed using a BD FACS LSR II flow cytometer (Becton Dickinson, Franklin Lakes, NJ). FlowJo software was used to analyze data. For intracellular IFNβ staining, surface-stained cells were fixed and permeabilized (Fix/Perm Wash Buffer, BioLegend, San Diego, CA), stained with anti-IFNβ (Abcam, Cambridge, MA), and followed by secondary antibody staining.

ELISA

Six million RAW 264.7 cells were plated in triplicate per well of a 24-well plate and treated with immuno-nanoparticles containing 20 μg/mL cdGMP, 17 μg/mL MPLA, or equivalent amounts of both cdGMP and MPLA. Cell culture supernatants were harvested 24 hr after seeding, clarified by centrifugation at 4° C., and analyzed per manufacturer's protocols for the presence of IFNα and IFNβ using LumiKine Xpress Bioluminescent cytokine ELISA kits from InvivoGen.

Immunostaining & Confocal Microscopy

4T1 tumor-bearing mice were injected with fluorescent nanoparticles and perfused 24 hr later with PBS and PBS containing 4% paraformaldehyde (Alfa Aesar, Haverhill, MA). Following euthanization, organs were harvested, fixed in 4% PFA/PBS, dehydrated in 30% sucrose/PBS, and embedded and frozen in OCT (Fisher Scientific, Hampton, NH). Primary (anti-CD31, anti-CD11c, anti-F4/80, anti-CD49b) and secondary antibodies were purchased from Thermo Fisher Scientific (Waltham, MA), Abcam (Cambridge, MA), and BioLegend (San Diego, CA). Frozen sections 10 m in thickness were stained with 1:100-1:150 primary antibodies overnight at 4° C., followed by staining with 1:100-1:150 secondary antibodies for 1 hr at 25° C. Stained sections were mounted with No. 1.5 glass coverslips using Vectashield DAPI aqueous mounting medium (Vector Laboratories, Burlingame, CA) and imaged using a Leica TCS SP8 gated STED confocal microscope (Leica Microsystems, Buffalo Grove, IL).

Transmission Electron Microscopy with Negative Staining

Carbon film grids were treated by glow discharge for 3 min. Liposomes were prepared in dilute suspensions (1:5-1:10 dilutions from treatment concentrations) and applied to treated grids and incubated for 30 s. Grids were washed 5× with 5 mM Tris buffer and directly afterwards stained 5× with 2% uranyl acetate. Imaging was performed using a Tecnai G2 SpiritBT electron microscope (FEI, Hillsboro, OR) operated at 80 kV.

Statistical Analysis

All statistical analyses are detailed in figure legends. Prism 7 (GraphPad Software) was used to analyze data by 1- or 2-way ANOVA with Tukey's or Sidak's post-test. P values less than 0.05 were considered statistically significant. Unless otherwise noted, all values are reported as the mean±standard error of at least 3 independent biological replicates. In animal studies, at least 5 mice were included in each group.

Results

Figure 2A:
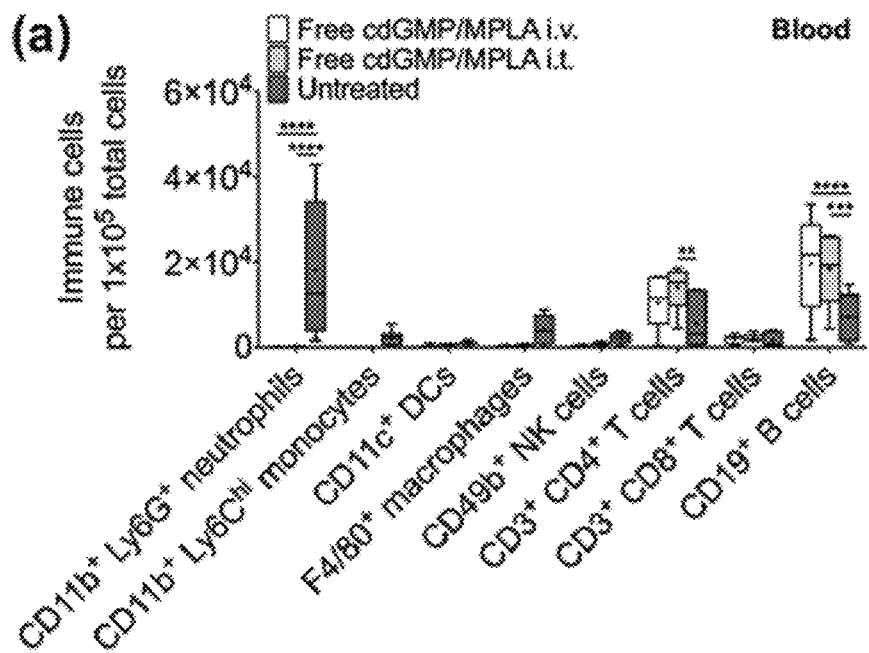
FIGS. 2(A-C) illustrate that treatment with free cdGMP and MPLA i.v. or i.t. does not elicit a sufficient immune response. Flow cytometry analysis of immune cells in the blood (A), tumor (B), and spleen (C) of 4T1 orthotopic mammary tumor-bearing mice 48 hr after treatment with 7 μg cdGMP and 6 μg MPLA i.v. or i.t. Treatment groups were made up of 5-6 mice (the untreated group contained 10-15 mice), data are plotted as box and whiskers plots (5-95 percentile, + designates the mean) with statistics by 2-way ANOVA with Tukey's post-test (* $P<0.05$,  $P<0.01$, * $P<0.001$, **** $P<0.0001$).
Figure 2B:
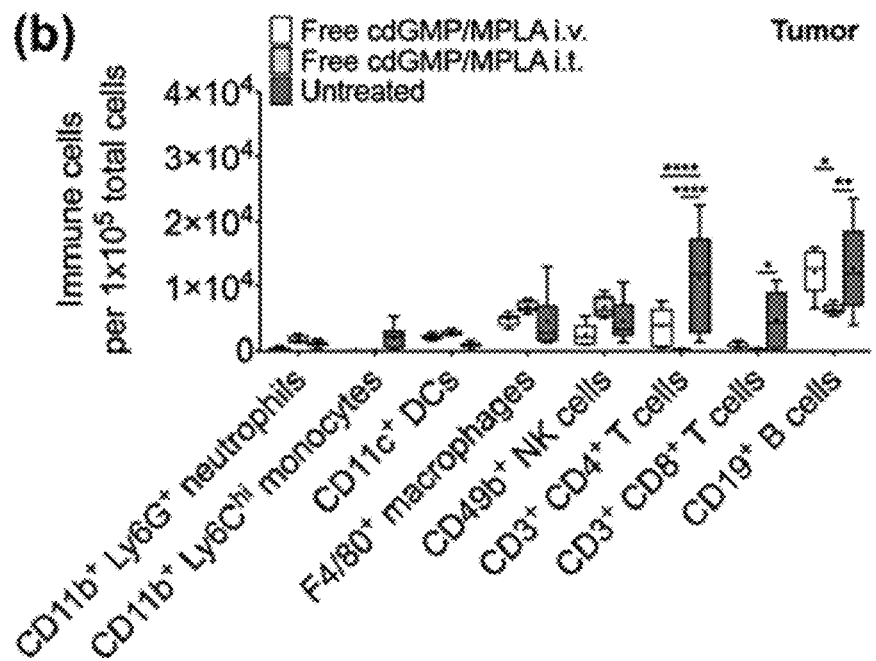
Figure 2C:
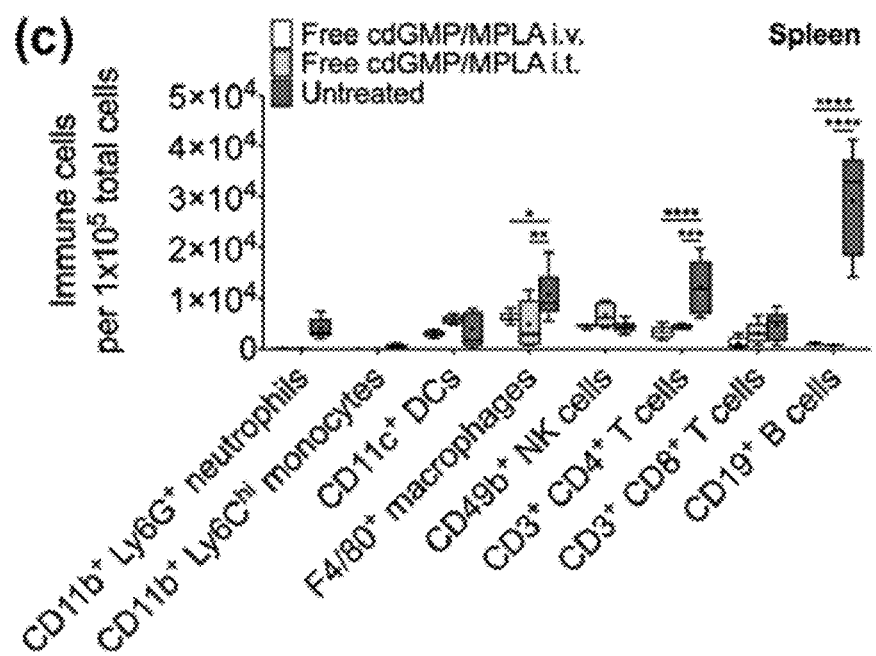

Immuno-Nanoparticles Mediate the Production of High Levels of IFNβ, are Stable In Vivo, and Drain with High Efficiency to Mammary Tumors To first define a quantitative rationale for our proposed systemic nanoparticle-mediated delivery platform, we investigated the mechanistic efficacy of delivering free immuno-agents both intravenously (i.v.) and intratumorally (i.t.) (FIG. 2). Importantly, while doses of up to 50 μg of free cdGMP administered i.t. are needed to regress early 4T1 primary tumors, to highlight a key advantage of nanoparticle encapsulation and systemic delivery, we elected to co-administer just 7 μg of free cdGMP and 6 μg of free MPLA i.v. or i.t., which are equivalent to doses that we aimed to deliver via immuno-NPs for therapeutic efficacy. Mice bearing orthotopic 4T1 primary tumors were treated with either free cdGMP and MPLA systemically (i.v.) or locally in the tumor (i.t.). Flow cytometry analysis 48 hr later indicated that there were no significant changes of major immune cell subsets in treated groups compared to controls in the blood (FIG. 2A), tumor (FIG. 2B), or spleen (FIG. 2C). In certain cases, immune cell populations decreased in treated mice compared to controls (i.e., blood neutrophils, tumor T and B cells, and splenic macrophages, CD4+ T cells, and B cells). Notably, a reduction in tumor infiltrating T cells is directly correlated to advanced disease and may be reflected in these free agonist treatments as early as 48 hr. These results strongly suggested that free cdGMP and MPLA delivered systemically or directly into the tumor had no therapeutic efficacy and clearly motivated the need for engineering a nanoparticle-mediated delivery strategy.

Figure 3A:
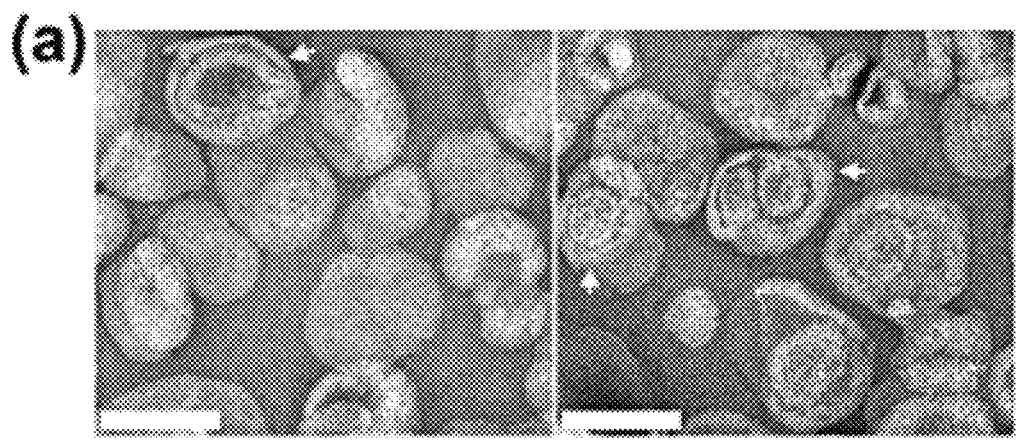
FIGS. 3(A-O) Illustrate that immuno-NPs are stable and function effectively to synergistically harness multiple innate immune pathways. Negative-stained TEM of immuno-liposomes (scale bars are 100 nm, white arrows note multilamellar nanoparticles) (A) DLS analysis for immuno-nanoparticle size (B) and zeta potential (C). Immuno-nanoparticle cdGMP encapsulation efficiency (D) and stability in terms of hydrodynamic size by DLS (E) and cdGMP release (F). Cartoon schematics of nanoparticle formulations used for ELISA analysis (G) for in vitro production of IFNβ (H). (I) Live-animal Spectrum imaging for tumor cell bioluminescence (left panel, units of radiance is photons/second) and DiD-labeled nanoparticle fluorescence (right panel, units of radiant efficiency are [photons/s]/[μW/cm2]) 24 hr after i.v. injection. Quantification of targeting from ex vivo organs and plasma of mice injected with fluorescent DiD-nanoparticles plotted as % dose per organ (J) at 4- and 28 hr post-injection i.v. Biodistribution at 28 hr is plotted as mean±standard error of % dose per organ (K) and % dose per gram tissue (L). ALT (M) and AST (N) measurements in enzyme units/L (dashed lines indicate average baseline levels of healthy mice) with corresponding mouse weight measurements (O) for N=5 mice per group. All conditions were performed at least in triplicate and plotted as mean±standard error with statistics by 1-/2-way ANOVA with Tukey's/Sidak's post-test (* $P<0.05$,  $P<0.01$, ** $P<0.0001$). DLS data are plotted as mean±standard deviation.
Figure 3E:
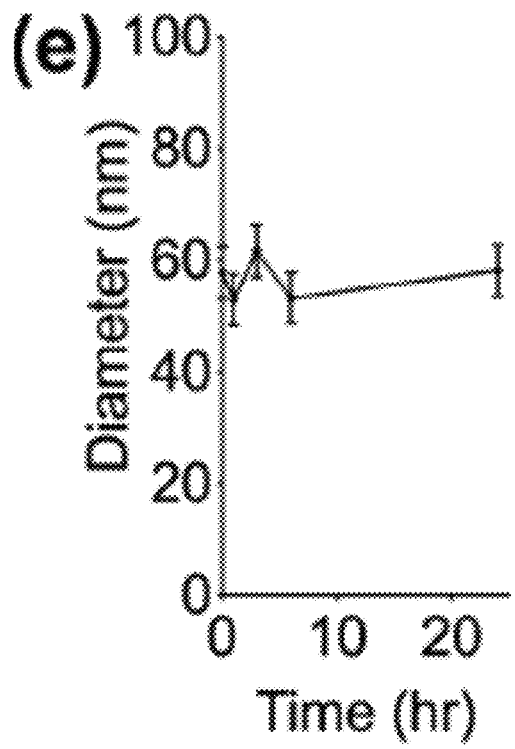
Figure 3F:
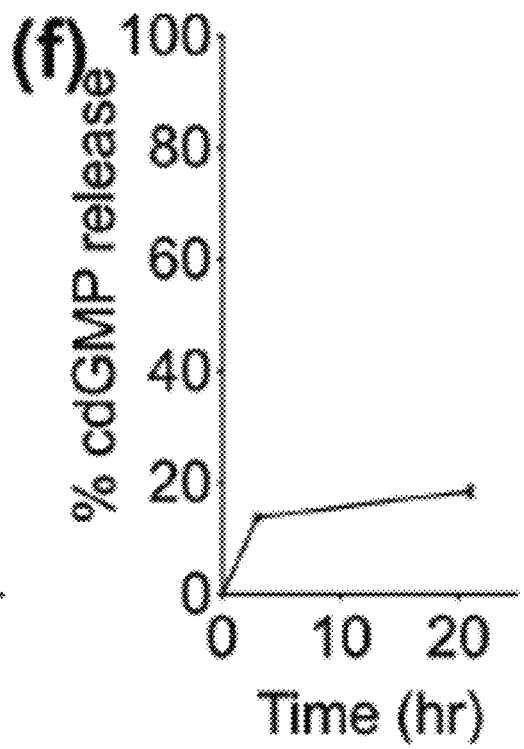
Figure 3G:
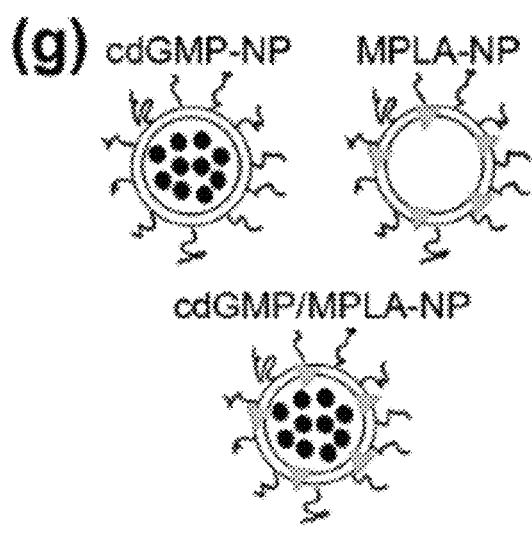

Towards this goal, we prepared about 60-nm liposomes containing equimolar quantities of DOPC and DPPC and 3 mol % mPEG2000-DSPE via ultrasonication. Transmission electron microscopy (TEM) was performed on negative-stained samples for analysis of lipid ultrastructure (FIG. 3A, white arrows indicate multilamellar nanoparticles). Dynamic light scattering (DLS) measurements indicated that nanoparticles were 61.2±13.4 nm in diameter (FIG. 3B) and zeta potential measurements indicated a neutral surface charge (−5.4±1.0 mV, FIG. 3C). Encapsulation efficiency of cdGMP was ~42% (FIG. 3D) and stability measurements indicated that hydrodynamic size remained the same over 24 hr (FIG. 3E). Release measurements of cdGMP at 37° C. demonstrated that 14% of cdGMP was released after 3 hr and just 19% was released over 21 hr, suggesting that high cdGMP payloads could be stably delivered to tumor sites (FIG. 3F). To validate the function of these nanoparticles, we treated RAW 264.7 macrophages in vitro with equivalent amounts of nanoparticles containing cdGMP only, MPLA only, and both cdGMP and MPLA on the same particle (FIG. 3G). Cell culture supernatants were assayed for levels of secreted IFNα and IFNβ (FIG. 3H) by ELISA after 24 hr.

Figure 3H:
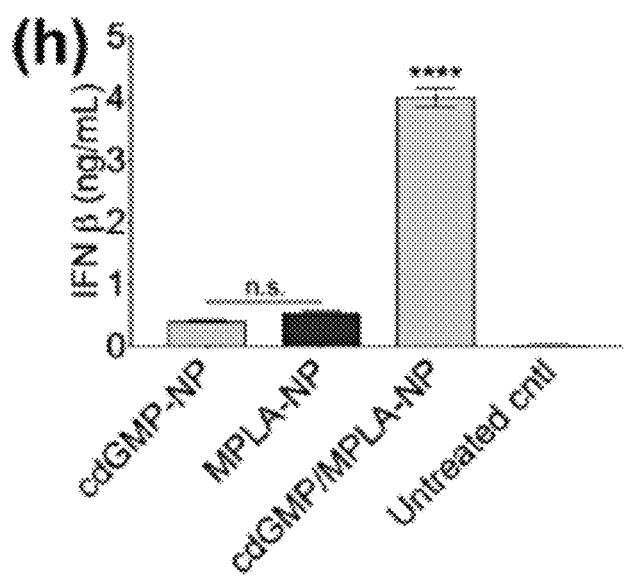

Both individual formulations mediated IFNβ production 19-25 times above background levels (FIG. 3H). Most significantly, however, immuno-NPs loaded with both cdGMP and MPLA induced a synergistic production of IFNβ that was 7-10 times the levels induced by nanoparticles carrying a single agonist alone (FIG. 3H). We therefore selected this co-loaded immuno-nanoparticle formulation for treatment studies in vivo.

Figure 3I:
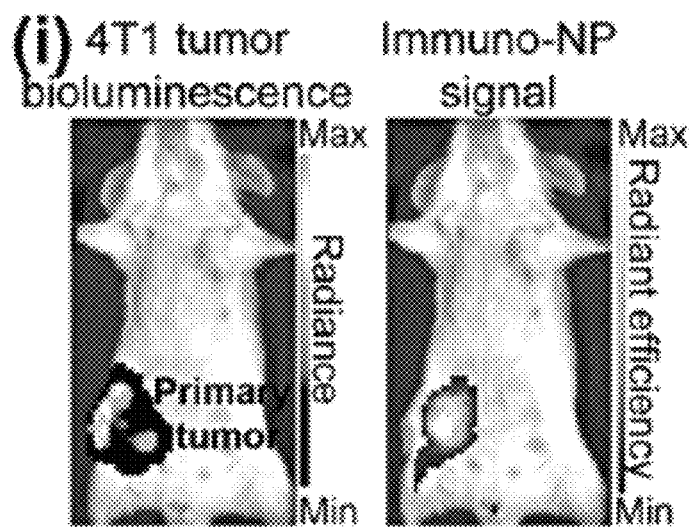
Figure 3J:
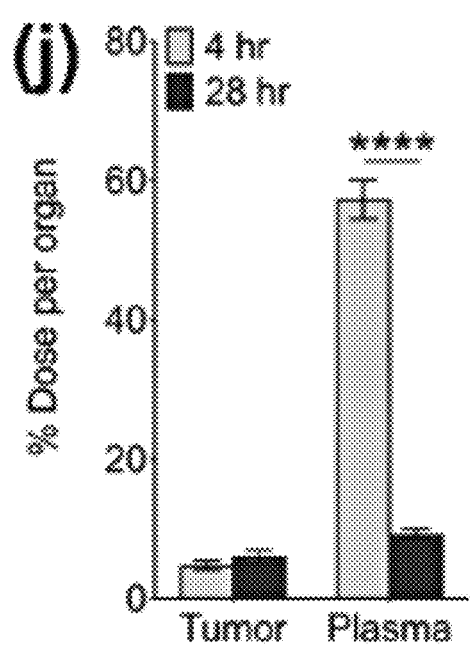
Figure 3K:
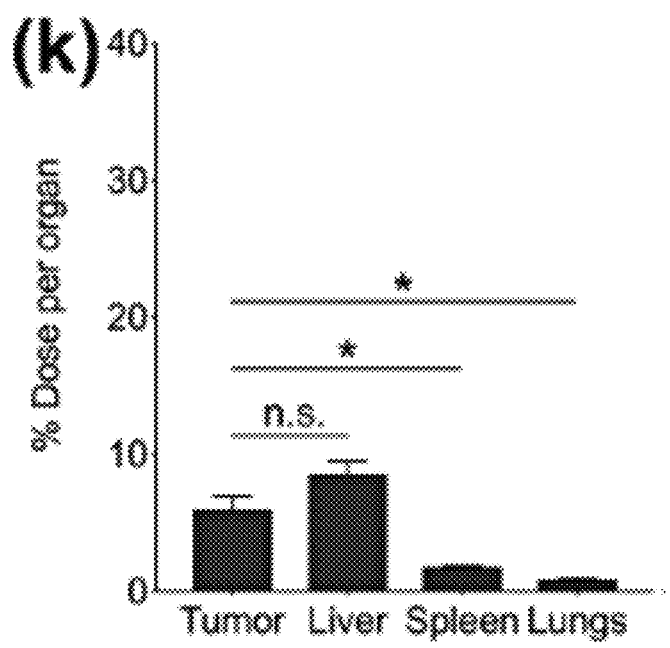
Figure 3L:
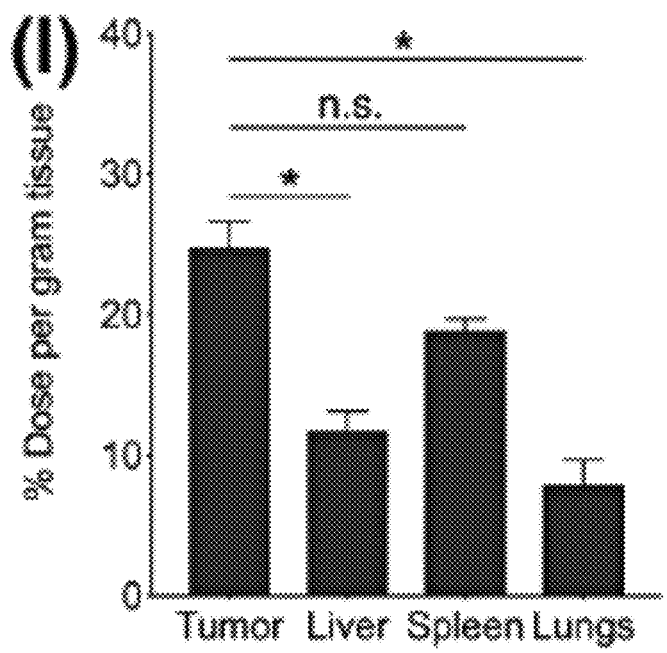
Figure 3M:
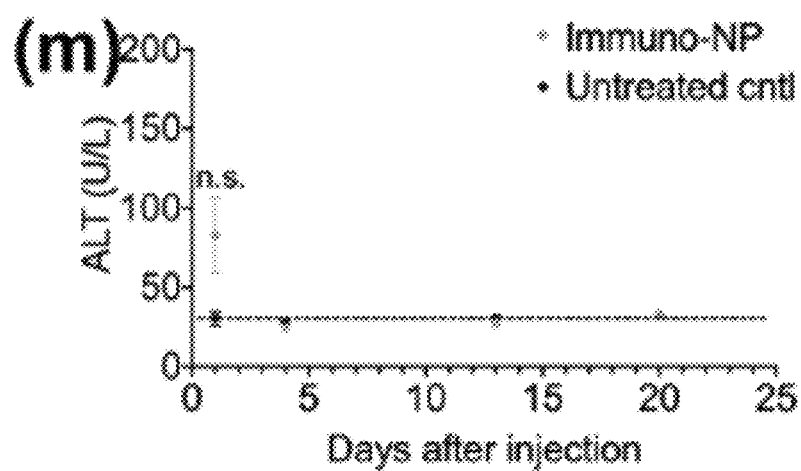
Figure 3N:
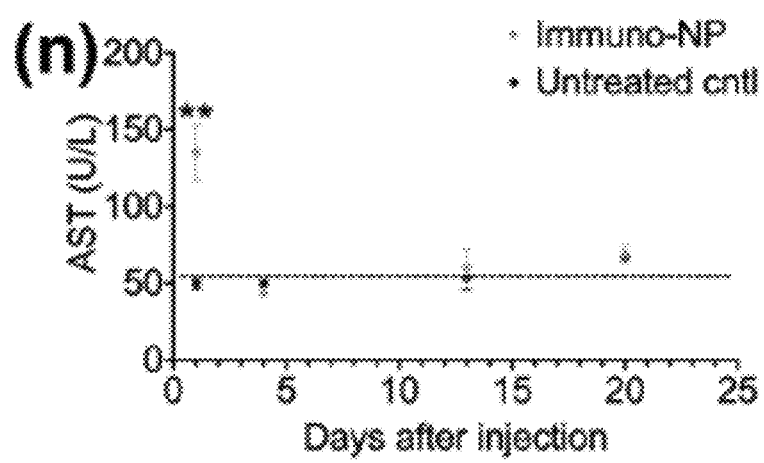
Figure 3O:
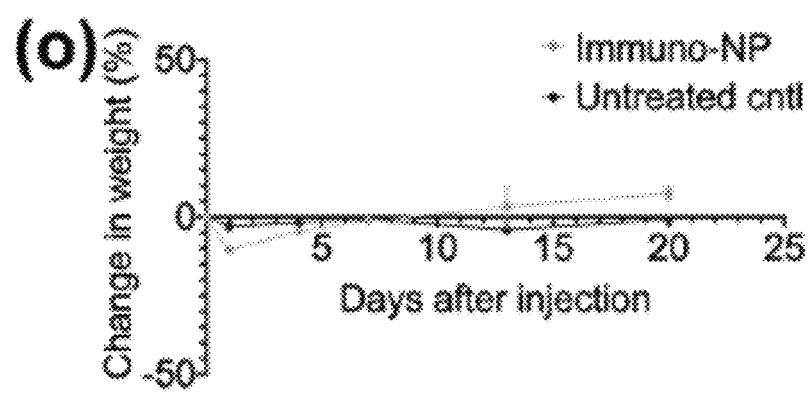
Figure 4A:
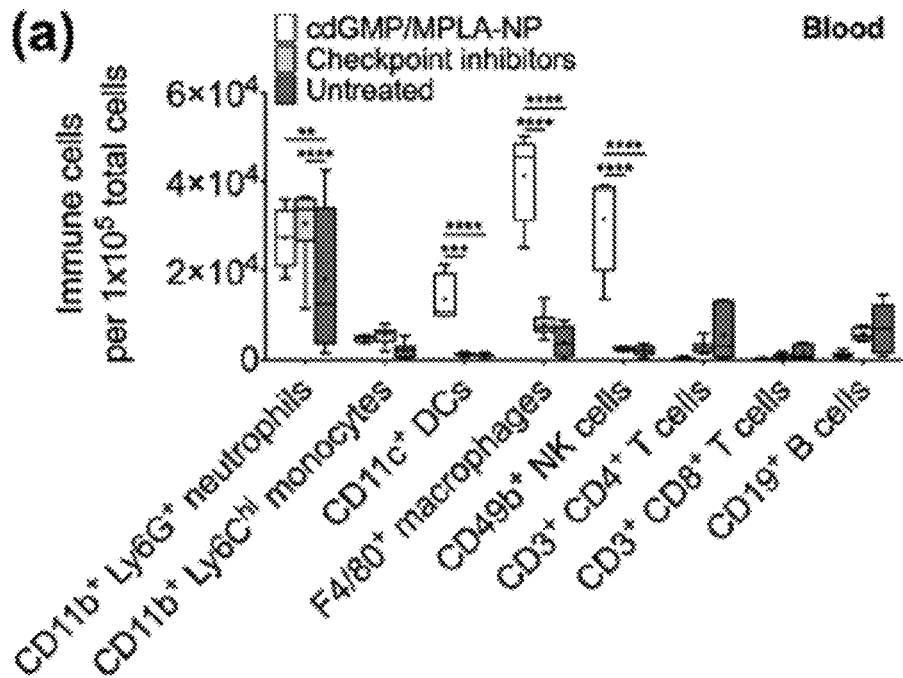
FIGS. 4(A-F) illustrate that treatment with immuno-NPs elicits a robust APC- and NK-cell-driven immune response. Flow cytometry analysis of immune cells in the blood (A), tumor (C), and spleen (E) of 4T1 orthotopic mammary tumor-bearing mice 48 hr after treatment with immuno-nanoparticles (carrying 7 μg cdGMP and 6 μg MPLA) i.v. or immune checkpoint inhibitors (250 μg anti-PD1 and 100 μg anti-CTLA4 i.v.). Representative flow cytometry dot plots for significant immune cell subtypes are shown for each tissue type blood (B), tumor (D), and spleen (F). Treatment groups were made up of 6 mice, data are plotted as box and whiskers plots (5-95 percentile, + designates the mean) with statistics by 2-way ANOVA with Tukey's post-test (* $P<0.05$,  $P<0.01$, * $P<0.001$, **** $P<0.0001$).
Figure 4B:
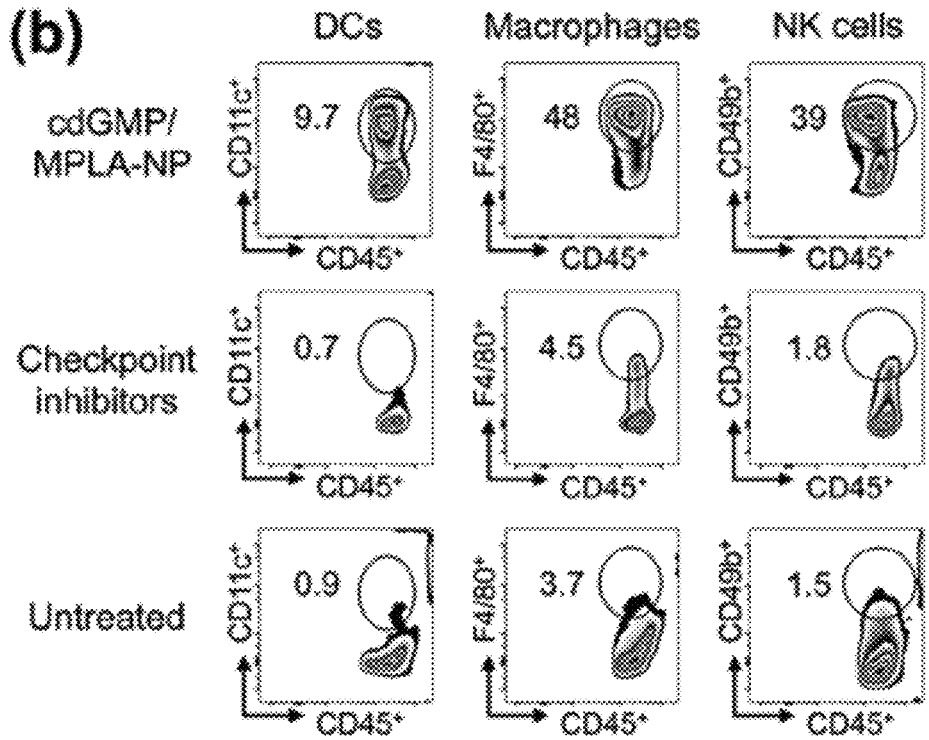
Figure 4C:
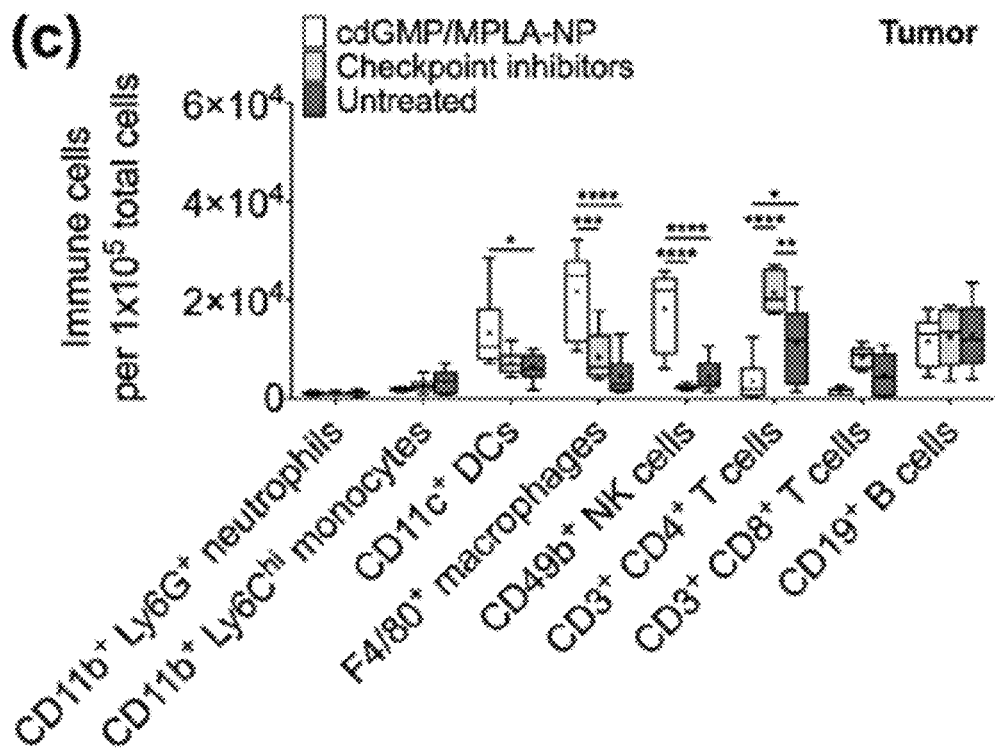
Figure 4D:
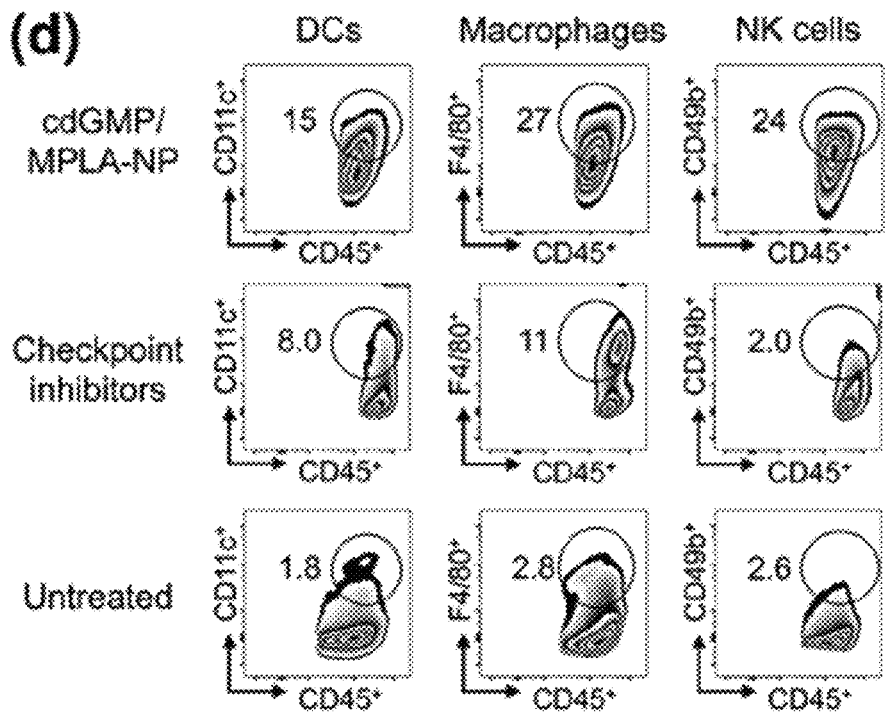
Figure 4E:
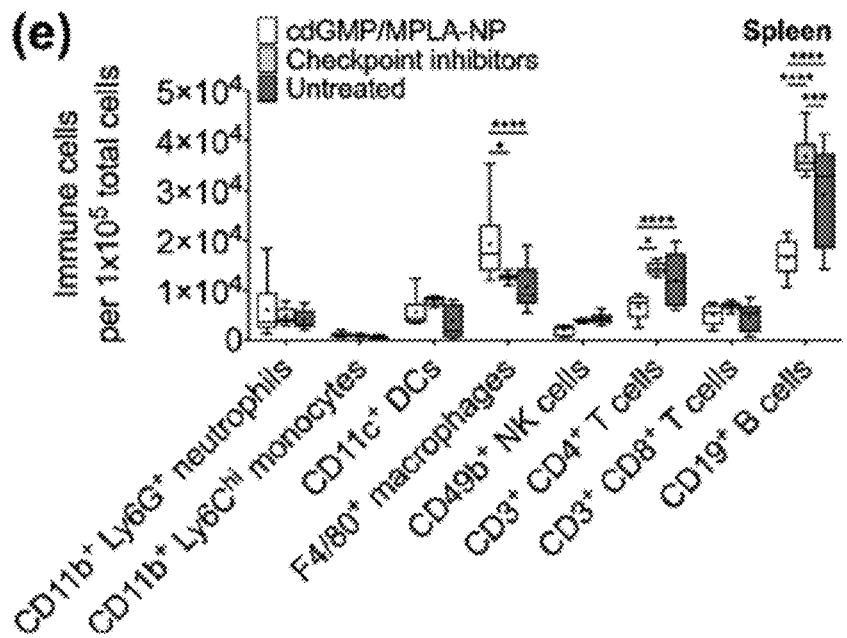
Figure 4F:
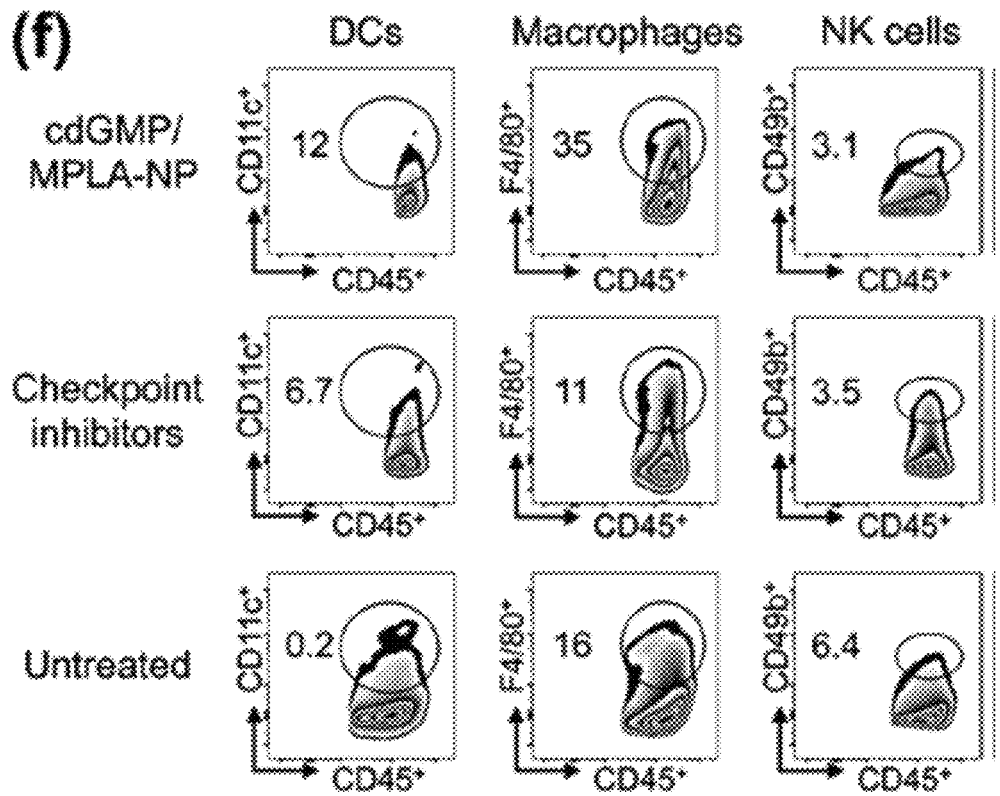

We next quantified tumor homing efficiency of immuno-NPs. Mice bearing orthotopic 4T1 primary tumors were injected with fluorescent nanoparticles and live-animal Spectrum imaging was performed 24 hr later (FIG. 3I). Particle fluorescence appeared brightest per pixel basis in the region of the primary tumor and was predominantly co-localized with luminescence from luciferase-expressing tumor cells, suggesting that immuno-NPs drained with high efficiency to the primary tumor site (FIG. 3I). FMT imaging on excised tumors indicated that particle signal appeared to collect in distinct nodes. To quantify tumor draining, 4T1 tumor-bearing mice were injected with fluorescent nanoparticles and perfused 4 hr and 28 hr later. Quantification of nanoparticle fluorescence obtained from Spectrum imaging indicated that 4.7% of immuno-NPs accumulated in tumor masses within 4 hr and this accumulation increased to 6.0% 28 hr post-injection (FIG. 3J). These data suggested that most of the tumor drainage occurred at a short time scale within hours after injection to the finite perivascular niche (FIG. 3J). Biodistribution analysis at 28 hr indicated that accumulation of immuno-NPs within the tumor compared to the liver, which is expected to have high retention due to its intrinsic clearance function, was similar per organ basis (FIG. 3K) and higher per gram tissue basis (FIG. 3L). Confocal microscopy analysis indicated that particles were found throughout the tissue from the tumor periphery to the center, often localizing in perivascular regions near the tumor vasculature as noted by CD31 staining for tumor endothelium. Notably, nanoparticle signal often appeared punctate within individual cells, reminiscent of endosomal localization. Taken together, these data suggested that immuno-NPs are stable and drained with high efficiency to primary mammary tumors within 4 hr. Since safety considerations are paramount for systemically administered therapies, we injected healthy mice that did not bear tumors with immuno-NPs and assayed serum levels of alanine aminotransferase (ALT, FIG. 3M) and aspartate aminotransferase (AST, FIG. 3N) as a metric of hepatotoxicity. While AST levels were significantly elevated compared to untreated controls 1 day post-treatment, they dropped back to baseline within just 4 days. While mice injected with immuno-NPs lost ~10% of their weight within 24 hr, they regained this weight within 7 days with an additional ~8% weight gain within 3 weeks compared to controls (FIG. 3O). We highlight therefore that any immuno-NP-mediated toxicity is minimal and transient, with recovery observed within just 4-7 days Immuno-Nanoparticle Treatment Mediates Upregulation of APCs and NK Cells We next performed flow cytometry analysis for the types of immune cells found both locally within the tumor as well as systemically in the blood and spleen 48 hr after treatment (FIG. 4). We used treatment with immune checkpoint inhibitors anti-programmed cell death protein-1 (anti-PD-1) and anti-cytotoxic T-lymphocyte-associated antigen-4 (anti-CTLA-4) as a metric of a clinically approved immunotherapy for comparison. Immuno-NP treatment very significantly increased DCs (11-13-fold), macrophages (5-10-fold), and NK cells (13-15-fold) in the blood compared to treatment with inhibitors and untreated controls (FIG. 4A). Similarly, immuno-NP treatment increased the number of DCs in the tumor 2.0-fold relative to untreated controls and also increased the numbers of tumor macrophages and NK cells 2.6-4.7-fold and 4.0-8.3-fold, respectively, compared to treatment with inhibitors and untreated controls (FIG. 4C). Immuno-NPs also increased numbers of splenic macrophages 1.5-1.8-fold compared to mice treated with inhibitors and control mice (FIG. 4E). Representative dot plots are shown for blood (FIG. 4B), tumor (FIG. 4D), and splenic (FIG. 4F) immune cells. The upregulation of APCs and NK cells in all three blood/tissue compartments suggested that immuno-NPs could mediate both an innate and adaptive immune response, which is important for long-term therapy. Notably, we also compared immune cell recruitment and activation with immuno-NPs that were actively targeted to unique molecules on the tumor-associated vasculature such as αvβ integrins and P-selectin but these formulations did not have significant upregulation of immune cells compared to controls 48 hr post-treatment. We deduced from these early findings that targeted NPs are likely to be sequestered at target sites that may not be enriched in APCs, while untargeted NPs are free to drain to the perivascular areas for ready uptake by APCs.

Figure 5D:
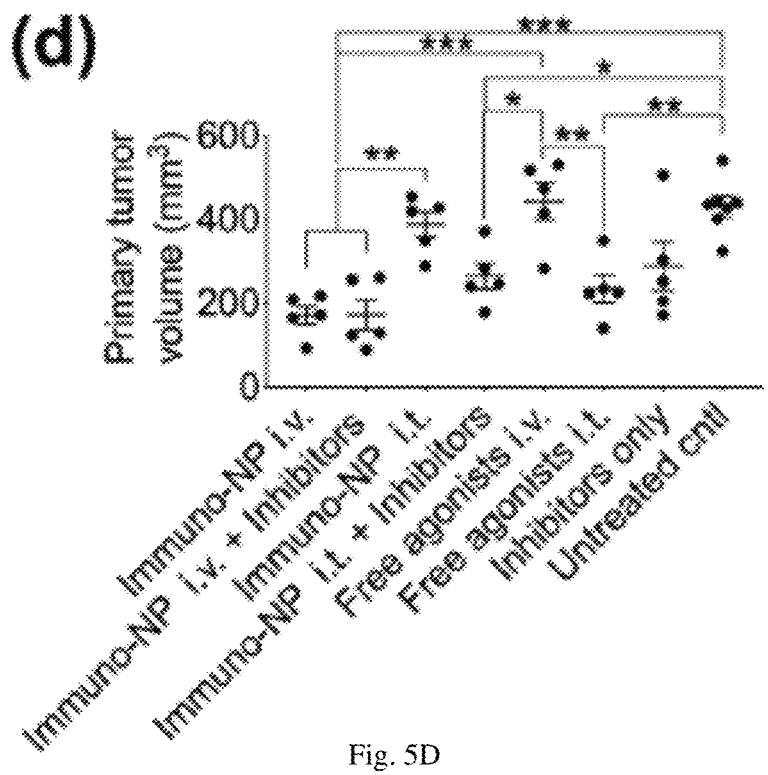
FIGS. 5(A-O) illustrate that immuno-NP treatment results in a substantial reduction in primary tumor mass with DC and NK cell effectors in the 4T1 model. (A) Representative bioluminescence images of 4T1 tumor-bearing mice from 3 treatment groups (immuno-NPs, empty NPs as vehicle control, and untreated controls) treated twice 2 days apart with tumors removed surgically 4 days after the start of treatment. Units of radiance are photons/s. Black arrows along x-axis designate treatment days. (B) Quantification of primary tumor cell luminescence as treatment was monitored. Nanoparticle groups had 5 mice per group while untreated control group had 3 mice. (C) Quantification of masses of excised tumors 4 days after the start of treatment. (D) Primary tumor volume measurements on day 5 after the start of treatment (N=5 mice per group). Flow cytometry analysis of immune cells per gram of tumor tissue (E), NP+ cells (F), NP signal per NP+ cell (G), and IFNβ per cell (H) (N=4 mice per group). Flow cytometry analysis of blood DCs (I), CD4+ T cells (J), and CD8+ T cells (K), and tumor DCs (L), NK cells (M), CD4+ T cells (N), and CD8+ T cells (O) (N=4 mice per group). Mean±standard error are plotted with statistics by 1-/2-way ANOVA with Tukey's post-test (* $P<0.05$,  $P<0.01$, * $P<0.001$).

Immuno-Nanoparticle Treatment Drives Reduction and Control of Primary Tumor Burden and Prevents Metastasis To determine the efficacy of immuno-NPs in reducing primary tumor burden, we treated mice bearing advanced 4T1 mammary tumors twice intravenously with immuno-NPs, as noted (FIG. 5A-B, black arrows indicate treatment days). Within a day, tumor signal in mice treated with immuno-NPs decreased by 85% while tumor signal in both control groups increased by 55-57%. Tumors were excised post-treatment and mice treated with immuno-NPs had tumors that were a significant 50-60% reduced in mass compared to either control group (FIG. 5C). Notably, there were no statistical differences in tumor masses between control groups indicating that the vehicle alone had no effect in mediating treatment efficacy (FIG. 5C). We then treated mice bearing 4T1 orthotopic tumors with immuno-NPs either i.v. or i.t. alone or supplemented with anti-PD-1 and anti-CTLA-4. We compared these treatment groups to control groups where mice were given either free cdGMP and MPLA i.v. or i.t., inhibitors only, or left untreated, black arrows indicate treatment days. A week after the start of treatment, mice given free immune agonists i.v. had to be euthanized due to large and ulcerating primary tumors. We noted that in the untreated control group, smaller tumor cell bioluminescence signals especially during the latter stages of therapy did not correlate to smaller tumor sizes as measured by physical caliper measurements (FIG. 5D), indicating, as has been widely shown in the literature, that the 4T1 tumor mass is composed of a highly heterogeneous mixture of cells where non-tumor cells infiltrating the TME are often involved in advancing the cancer. From the start of treatment and up to one week afterwards, tumors of mice treated with immuno-NPs i.v. alone or with inhibitors significantly remained the smallest with volumes of ~170 mm3 (data for day 5 post-treatment in FIG. 5D).

Figure 5E:
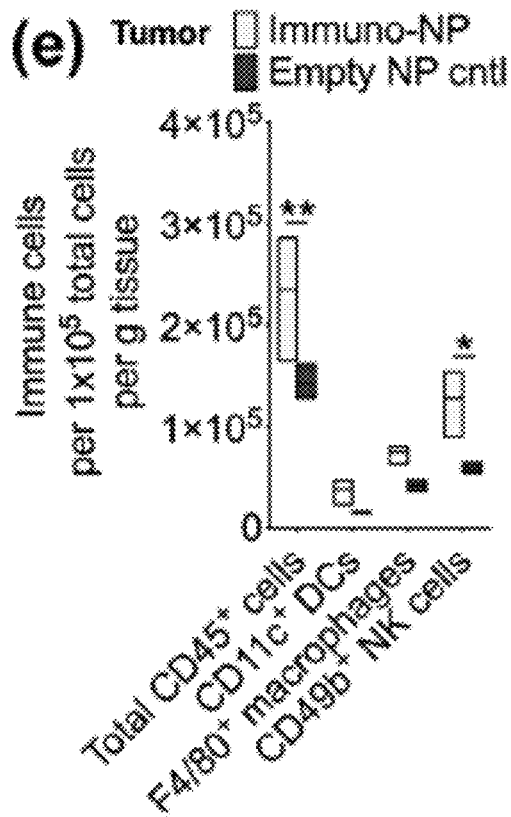
Figure 5F:
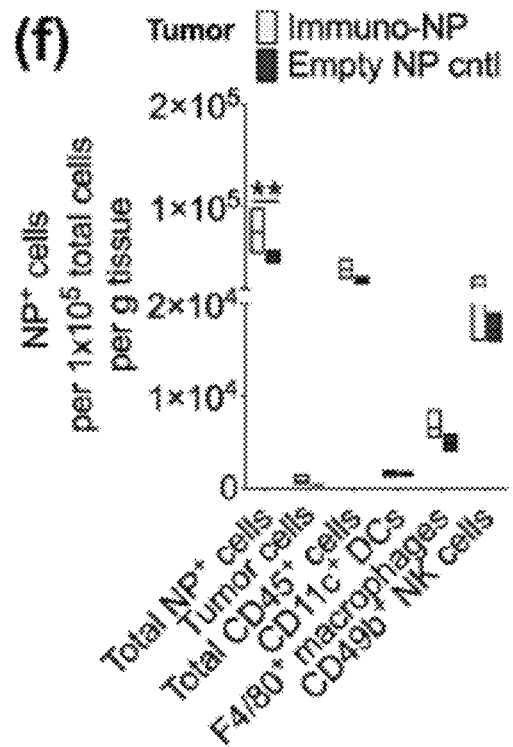
Figure 5G:
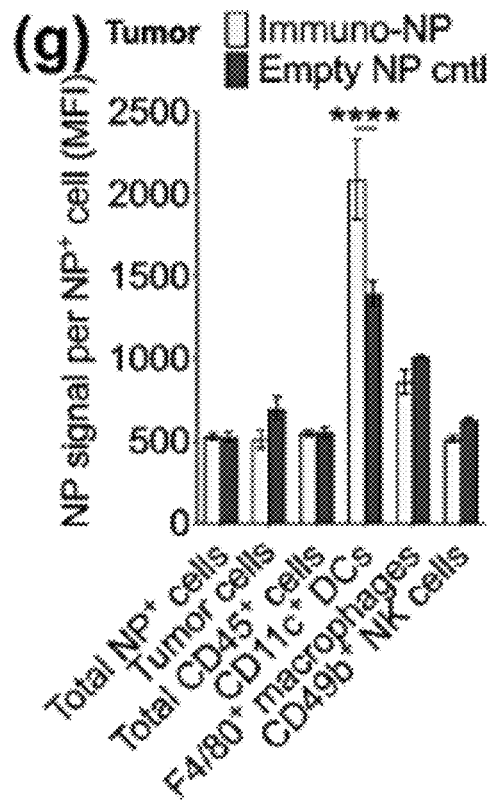
Figure 5H:
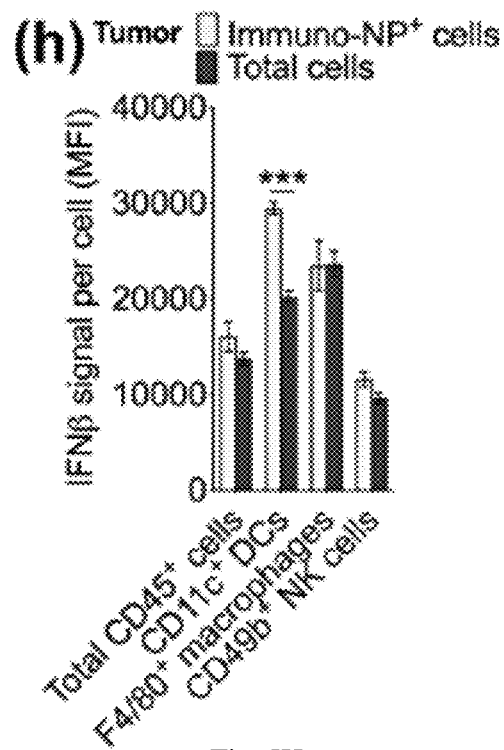
Figure 5I:
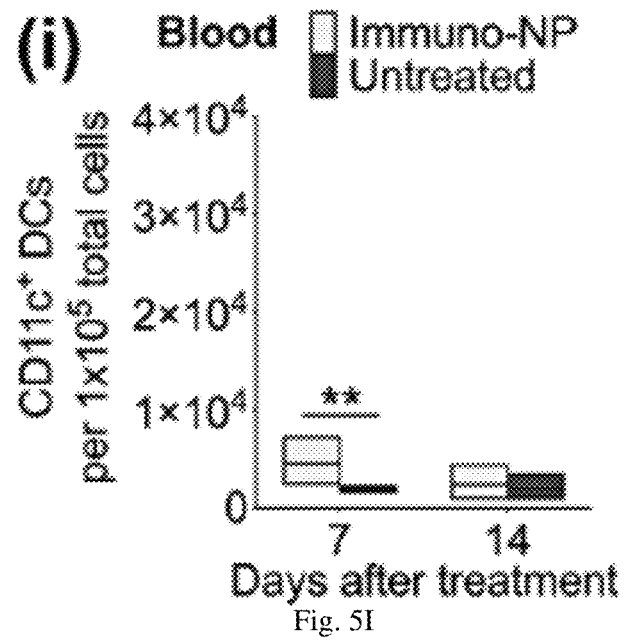
Figure 5J:
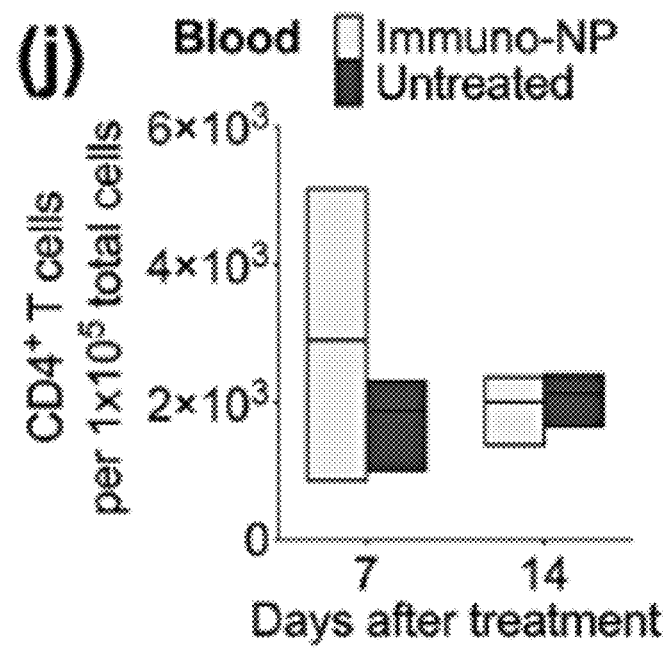
Figure 5K:
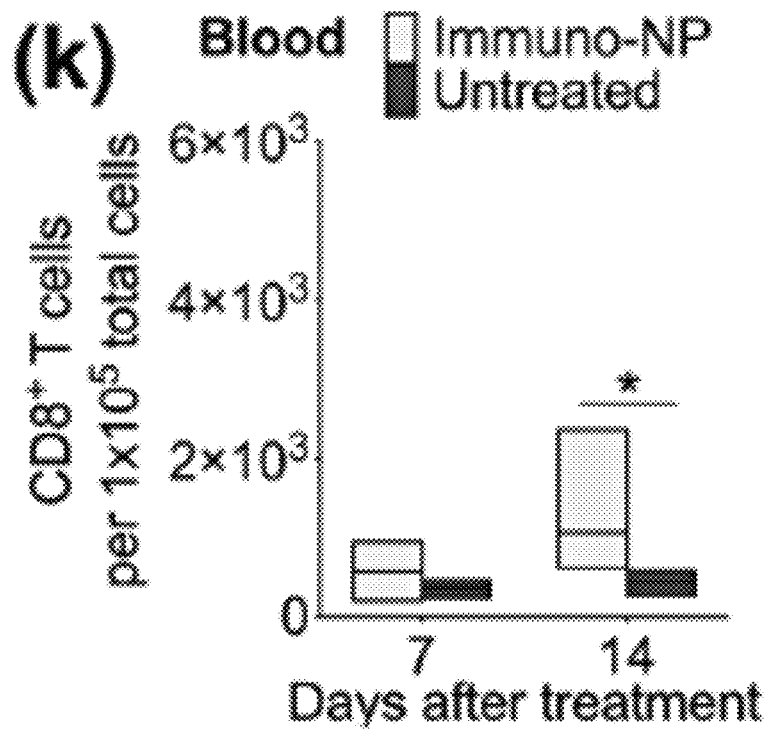
Figure 5L:
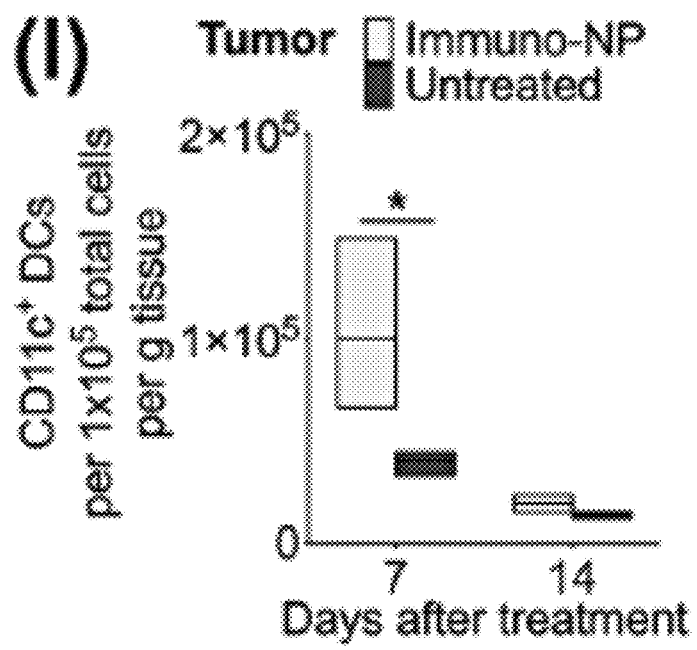
Figure 5M:
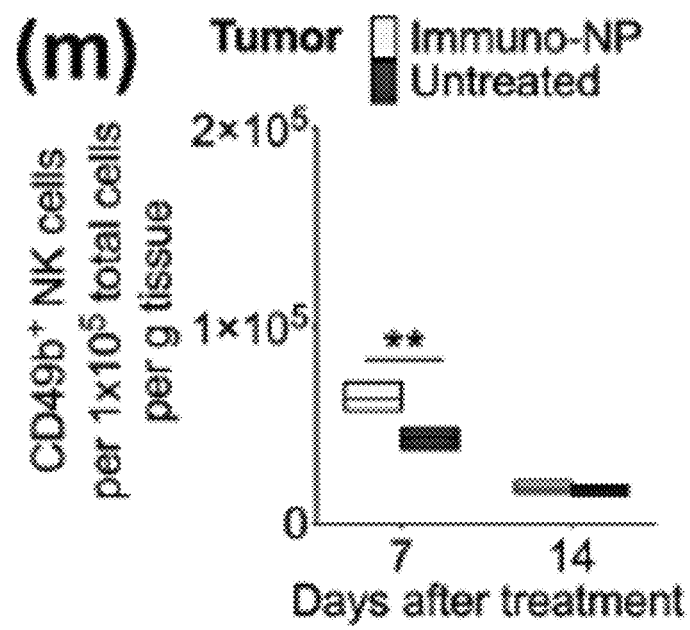
Figure 5N:
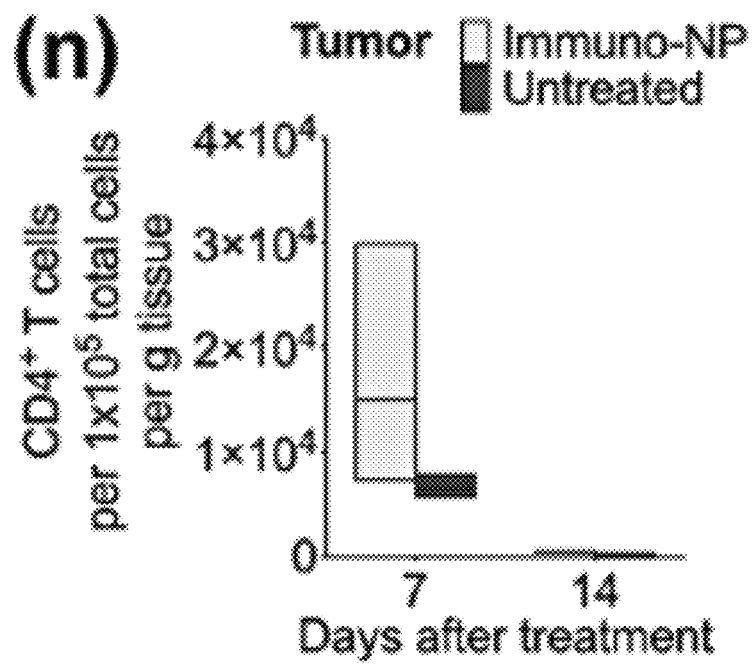
Figure 5O:
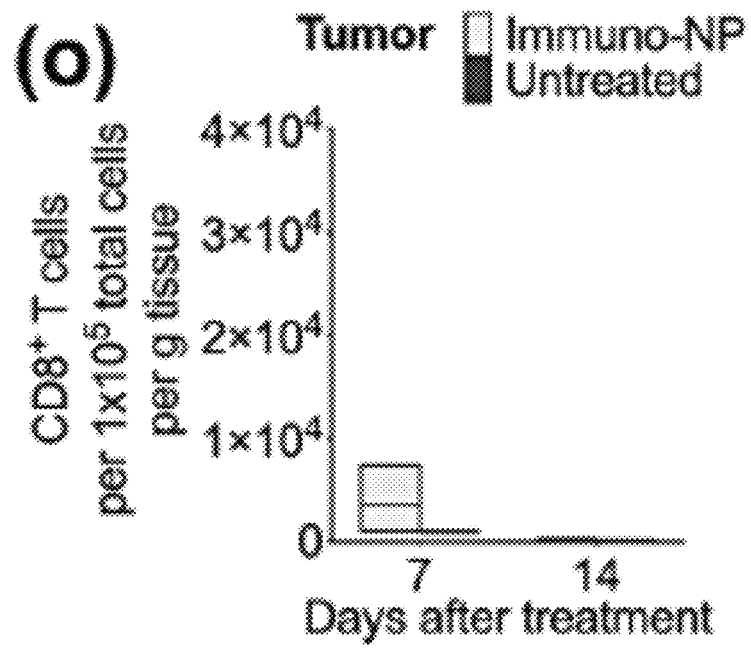

To establish a mechanistic framework for immuno-NP uptake and function within the primary tumor, we next treated 4T1 tumor-bearing mice with two consecutive daily doses of fluorescent immuno-NPs and analyzed for cellular uptake by flow cytometry. Compared to mice injected with empty NPs, mice treated with immuno-NPs had significantly elevated numbers of CD45+ immune cells and NK cells per gram of tumor tissue (FIG. 5E). Further, there was a significantly increased number of cells that had taken up NPs in these treated mice, while levels of uptake within tumor cells, CD45+ immune cells, DCs, macrophages, and NK cells were statistically similar (FIG. 5F). Notably, while ~53% of NPs were taken up by CD45+ immune cells (~3% by DCs, ~9% by macrophages, and ~33% by NK cells), only ~0.9% of NPs were taken up by tumor cells, indicating that perivascular accumulation was optimal for targeting of APCs and NK cells in lieu of tumor cells, since this niche is enriched for these immune cells (FIG. 5F). Further analysis also demonstrated that DCs in particular endocytosed significantly more immuno-NPs within the primary tumor (FIG. 5G), and that these NP+ DCs produced significantly more IFNβ (FIG. 5H). To investigate longer-term efficacy, blood and tumors were harvested from these mice 7 and 14 days post-treatment and assayed for immune cell content by flow cytometry. Compared to untreated controls, DCs (FIG. 5I) and CD8+ T cells (FIG. 5K) were significantly elevated in the blood 7 and 14 days post-treatment, respectively, with no statistical differences in CD4+ T cells (FIG. 5J). Intratumoral DCs (FIG. 5L) and NK cells (FIG. 5M) were similarly elevated per gram of tumor tissue 7 days post-treatment, with no statistical differences in numbers of intratumoral T cells (FIG. 5N-0).

Figure 6A:
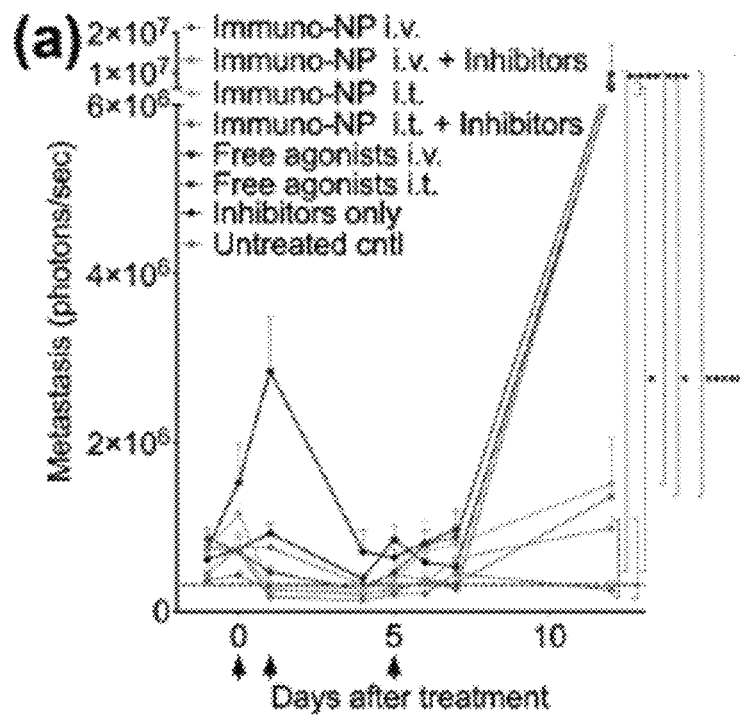
FIGS. 6(A-J) illustrate that immuno-NPs mediate the prevention of metastasis in the 4T1 model. (A) Bioluminescence quantification of lung/lymph node metastasis signal for each treatment group (N=5-7 mice per group). Black arrows along x-axis designate treatment days. (B) Representative bioluminescence images of metastasis. Units of radiance are photons/s. Flow cytometry analysis of immune cells per gram of tumor tissue (C), NP+ cells (D), representative dot plots (E), NP signal per NP+ cell (F), and IFNβ per cell (G) (N=4 mice per group). Mean±standard error are plotted with statistics by 1-/2-way ANOVA with Tukey's post-test (* $P<0.05$,  $P<0.01$, * $P<0.001$, *** $P<0.0001$). Confocal microscopy of metastatic lung tissue sections with staining for DCs (H), macrophages (I), and NK cells (J). White arrows indicate areas with immuno-NPs. Scale bars are 100 μm.
Figure 6B:
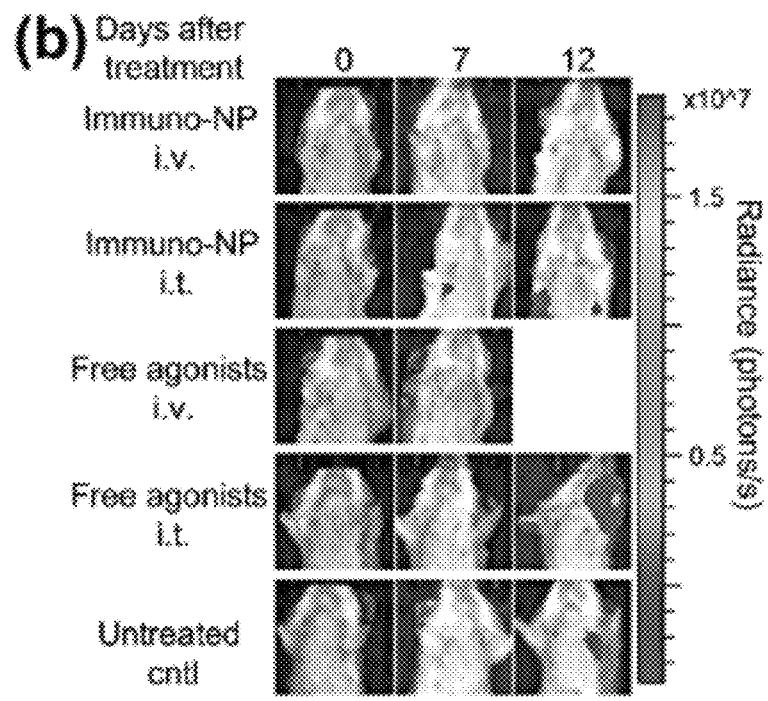
Figure 6C:
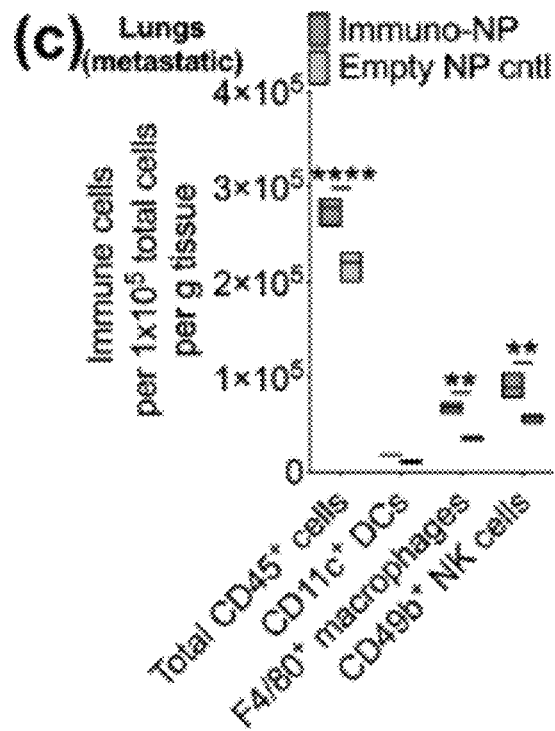
Figure 6D:
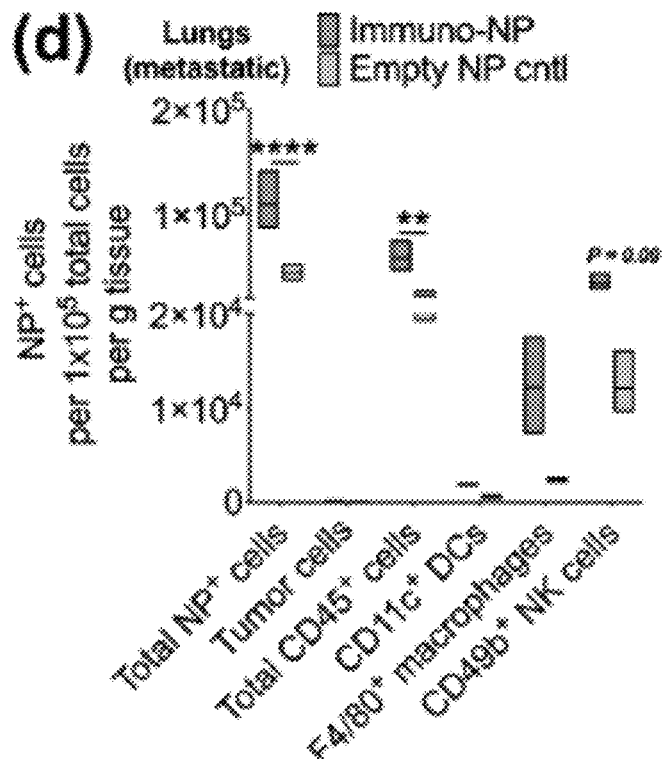
Figure 6J:
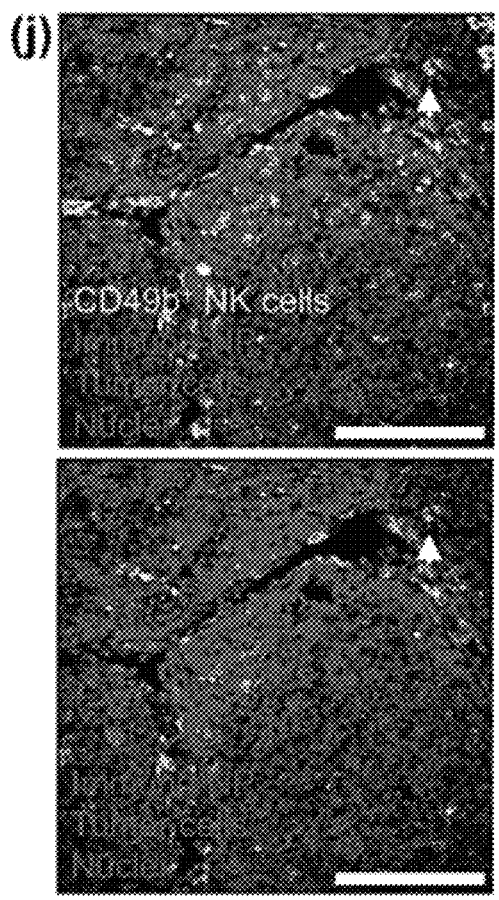
Figure 7A:
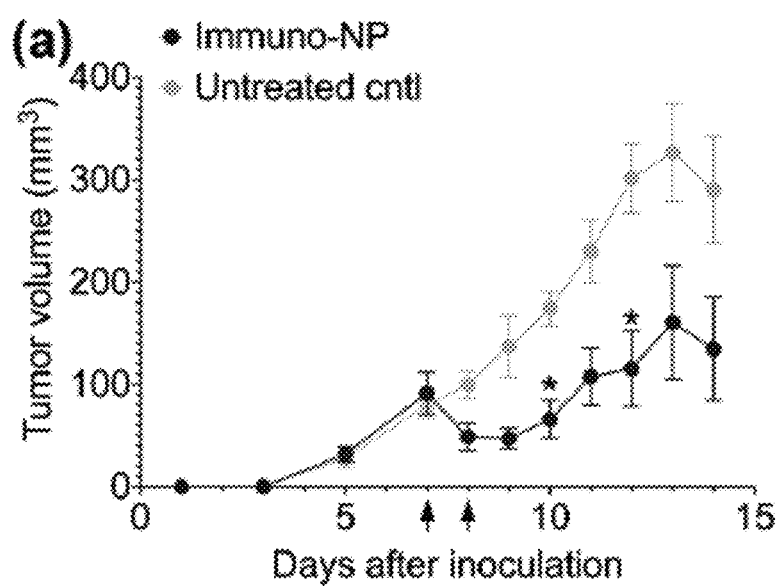
FIGS. 7(A-F) illustrate that immuno-NP treatment has significant efficacy in the treatment of B16F10 melanoma. (A) Tumor volume measurements, where black arrows on x-axis designate treatment days (N=5 mice per group). (B) Kaplan-Meier survival analysis. Flow cytometry analysis for blood DCs (C), NK cells (D), CD4+ T cells (E), and CD8+ T cells (F). Mean±standard error are plotted with statistics by 1-/2-way ANOVA with Tukey's post-test (* $P<0.05$, *** $P<0.001$).
Figure 7B:
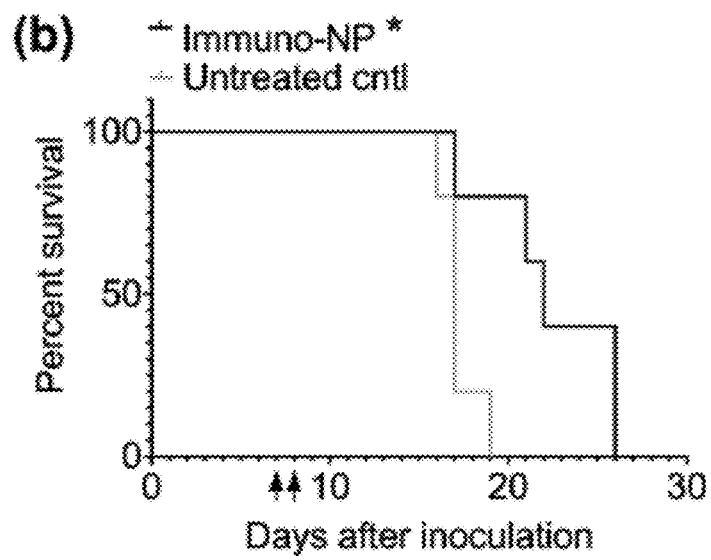
Figure 7C:
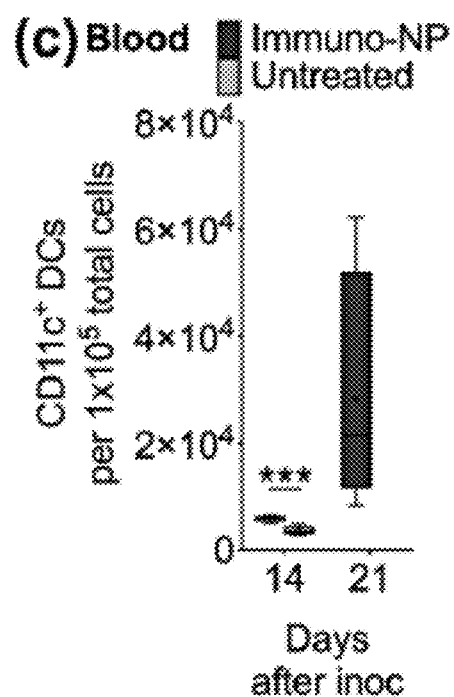
Figure 7D:
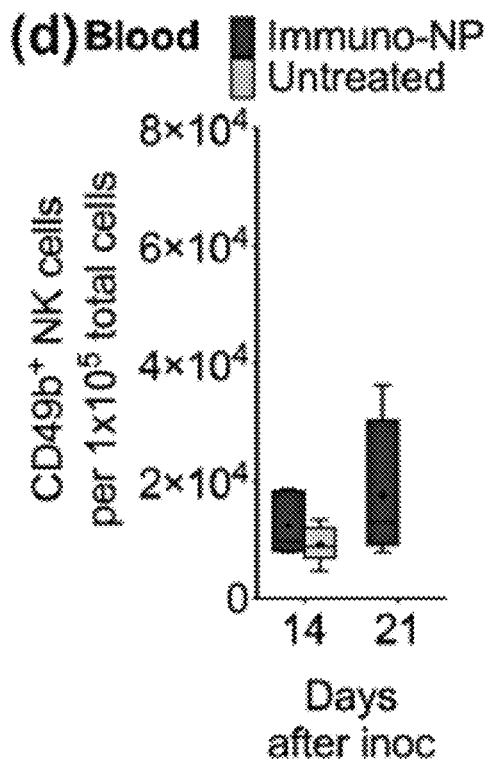
Figure 7E:
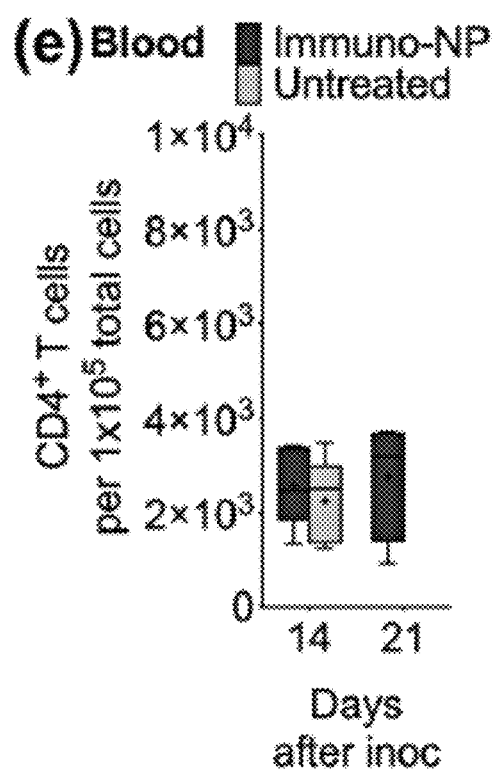
Figure 7F:
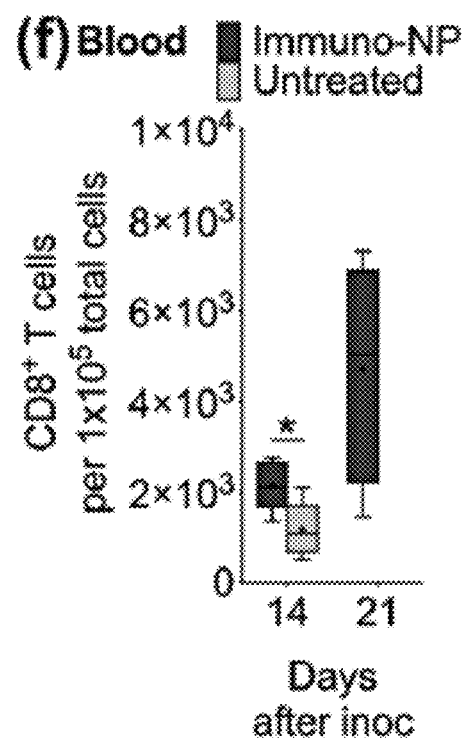

To determine the efficacy of immuno-NPs in treating metastasis, we treated 4T1 tumor-bearing mice with immuno-NPs with and without checkpoint inhibitors i.v. or i.t. and free agonists i.v. or i.t. (FIG. 6A, black arrows indicate treatment days). From all the formulations, it was only immuno-NPs administered i.v. that completely prevented metastasis in the lungs and lymph nodes (FIG. 6A). Twelve days after the start of treatment, metastatic signal in mice treated with immuno-NPs i.v. remained near baseline and significantly lower than signal in mice treated with free agonists i.t., immuno-NPs i.t. with inhibitors, and inhibitors only (FIG. 6A; representative bioluminescence images of metastasis shown in FIG. 6B). Notably 12 days post-treatment, while none of the mice treated with immuno-NPs i.v. had a metastatic signal above threshold (dashed grey line in FIG. 6A), 50-100% of mice in all other groups had increased signal. As with the primary tumor, we then sought to establish a mechanistic framework for immuno-NP uptake and function within lungs that contained metastases. To this end, we treated 4T1 tumor-bearing mice with two consecutive daily doses of fluorescent immuno-NPs and analyzed for cellular uptake by flow cytometry. Compared to mice injected with empty NPs, mice treated with immuno-NPs had significantly elevated numbers of CD45+ immune cells, macrophages, and NK cells per gram of lung tissue (FIG. 6C). There were significantly more cells in treated mice that had taken up NPs (FIG. 6D) and while ~53% of these NP+ cells were CD45+ immune cells (and significantly so), only ~0.2% of cells that had taken up NPs in the lungs were tumor cells (FIG. 6D). Representative flow cytometry dot plots for NP+ cells are shown in FIG. 6E. Strikingly, in mice that were treated with immuno-NPs, lung DCs and macrophages had endocytosed significantly more NPs (FIG. 6F) and these NP+ DCs and macrophages produced significantly more IFNβ (FIG. 6G). Confocal microscopy studies indicated that immuno-NPs were found largely in the vicinity of tumor cells in the lungs and in close proximity to DCs (FIG. 6H), macrophages (FIG. 6I), and NK cells (FIG. 6J), indicating that this immune response was tumor-associated and not non-specific. In areas of the lungs that did not contain metastases, immuno-NPs were also largely absent.

Finally, to establish the broader impact of the efficacy of this immuno-NP treatment to other aggressive cancers, we investigated their therapeutic efficacy in the treatment of mice bearing orthotopic B16F10 melanoma tumors (FIG. 7). We treated tumor-bearing mice with two consecutive daily doses of immuno-NPs and observed that tumor volume dropped by 50% in treated mice compared to controls within a single day and continued to remain a significant 50-65% reduced over the course of 2 weeks (FIG. 7A, black arrows indicated treatment days). Survival in treated mice was also significantly increased compared to controls (FIG. 7B). Blood flow cytometry analysis indicated significantly elevated levels of DCs (FIG. 7C) and CD8+ T cells (FIG. 7F) even 7 days post-treatment. Notably, numbers of blood DCs and CD8+ T cells continued to increase 14 days post-therapy. There were no statistical differences in levels of blood NK cells (FIG. 7D) and CD4+ T cells (FIG. 7E). Taken together, these results indicate that the therapeutic efficacy of immuno-NPs can be translated across multiple models of aggressive cancer.

While immune agonists can generate powerful anti-tumor immunity, their successful delivery to the TME relies on efficiently accessing the tumor microvasculature, minimizing off-target toxicity, and, in the case of multiple synergistic therapeutics, targeting the same cell. Here, we elected to co-encapsulate STING agonist cdGMP and TLR4 agonist MPLA within a single liposomal nanoparticle and exploited systemic delivery to access the leaky tumor microvasculature in entirety. Our delivery strategy mediated preferential collection within the perivascular areas of the TME that are rich in APCs. Co-encapsulation within a nanoparticle not only prevents cdGMP/MPLA-induced off-target systemic toxicity, but also guarantees delivery to the same target APCs. In the case of the primary tumor, systemic delivery enables immuno-NP accumulation within the APC-rich perivascular areas of the tumor, which can drive preferential accumulation of immuno-NPs within CD45+ immune cells compared to tumor cells. Given that both cdGMP and MPLA are strong inducers of Type I interferons and share common downstream effectors such as NF-$_K$B and IRF3, the IFNβ synergy we measured as a result of co-encapsulation of both agonists is likely due to amplification of these downstream pathways. IFNβ drives robust innate immunity, NK cell activity, and APC-mediated activation of CD8+ T cells. It is also pivotal in preventing malignant transformation and de-differentiating cancer stem cells.

Our mechanistic analysis has demonstrated that treatment efficacy depends on the accumulation of immuno-NPs at the site of the primary tumor or metastases, their uptake by local APCs, and the production of IFNβ by these cells. Notably, we have shown these APCs endocytose a significantly greater number of immuno-NPs. We also observed significantly increased levels of blood CD8+ T cells in mice treated with immuno-NPs, indicating a functioning vaccination mechanism, where activated tumor-resident DCs can travel to lymph nodes to prime systemic T cells and mediate their recruitment back to the site of the tumor. These data further demonstrate that NK cells are a significant contributor to efficacy, and their role is highly advantageous since they are not only direct-killing initial responders but can also be involved in the formation of memory NK cells.

In conclusion, we have constructed a versatile lipid-based immuno-NP platform that serves to mount a robust anti-tumor immune response by accumulating with high efficiency in the APC-rich perivascular regions of primary tumors and metastases and inducing the strong production of IFNβ. We have shown that synergy between cdGMP and MPLA co-encapsulated in the same nanoparticle drives the production of high levels of IFNβ and mediates a robust APC- and NK cell-driven anti-tumor immune response. Finally, we have shown that immuno-particles delivered systemically via the vasculature outperform even intratumoral delivery and serve to reduce and limit the growth of the primary tumor and prevent metastasis without the need for additional supplementation with clinically approved checkpoint inhibitors. This nanotechnology platform serves to effectively reverse significant TME immunosuppression.

Example 2

Figure 8A:
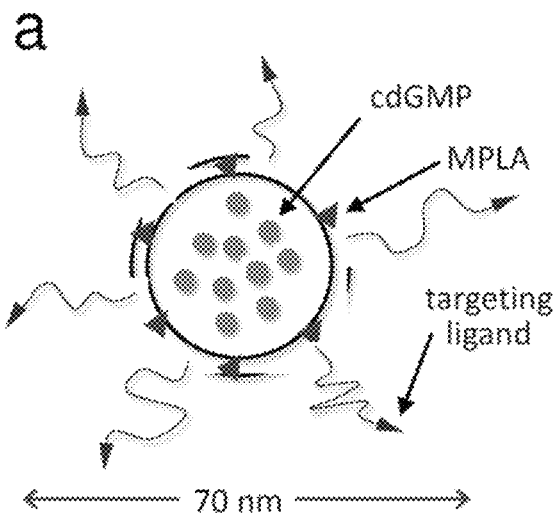
FIGS. 8(A-C) are an illustration of the targeted immuno-nanoparticle platform that shows (A) the nanoparticle loaded with the dual cargo of MPLA and cdGMP, (B) the synergy of the STING agonist (cdGMP) and TLR4 agonist (MPLA) to activate the signaling pathways leading to the induction of potent cytokines including the type I interferons (IFNs), and (C) the targeting scheme to direct the immuno-nanoparticle to APCs in the near-perivascular TME of early metastasis.
Figure 8B:
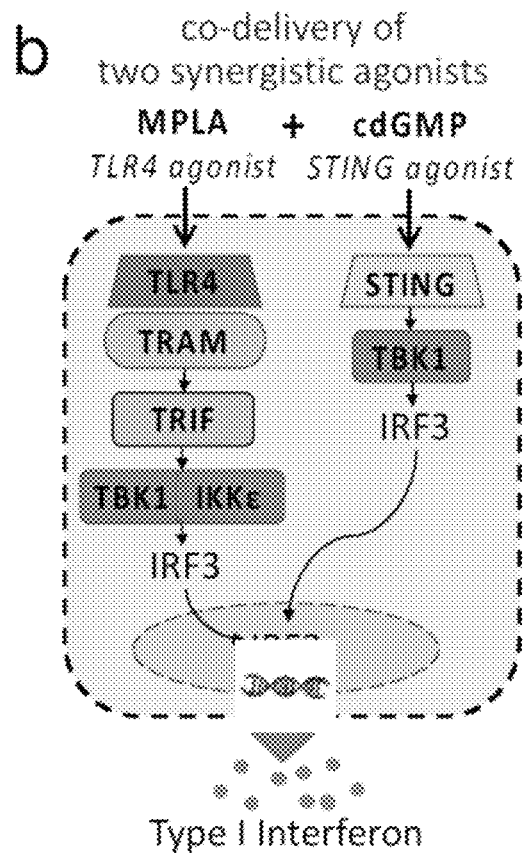
Figure 8C:
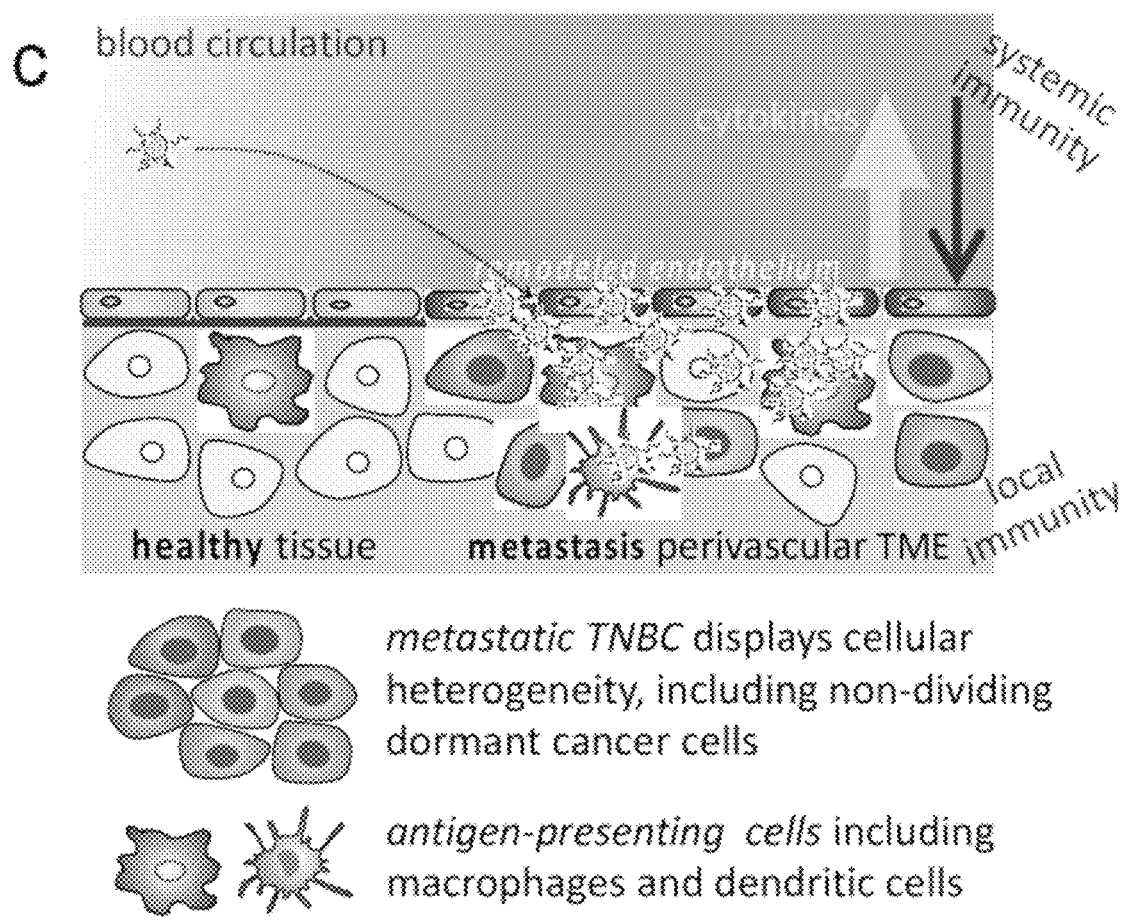

Considering that metastatic triple negative breast cancer's (mTNBC's) tumor microenvironment (TME) is poorly immunogenic with profound immunosuppression, effective tumor site-specific immunity heavily depends on the robust activation of local antigen-presenting cells (APCs), such as dendritic cells (DCs) and macrophages. An overview of a novel approach we have developed to promote interferon β-driven anti-tumor immunity is illustrated in FIG. 8. Conventional strategies focus on a single, mono-functional immune modulator. Nanoparticles, by contrast, can simultaneously deliver multiple therapeutics (FIG. 8A). To create a robust immune-potentiating stimulus to drive a sustainable, self-amplifying antitumor immune response, we have targeted two innate immune pathways by co-delivering two agonists (FIG. 8B), that when combined exhibit a synergistic effect on the induction of Type I interferons (IFN). To guarantee uptake of both agonists by the same antigen-presenting cell (APC), both agonists are co-loaded in the same nanoparticle. Since traditional lymph node or local intratumoral administration of immune agonists is limited to patients with accessible primary tumors, systemic administration has significant advantages in the case of metastasis. Systemic administration enables the nanoparticles to efficiently spread throughout the microvasculature, seek regions of remodeled endothelium and readily gain access within the APC-rich perivascular areas of metastasis (FIG. 8C).

Immuno-Nanoparticle Design
Driving a TME-Specific Anti-Tumor Immune Response Via Co-Delivery and Synergy of a STING Agonist and a TLR4 Agonist By harnessing multiple overlapping innate immune pathways, a more potent, synergistic cytokine response is triggered. The immuno-nanoparticle is co-loaded with cyclic diguanylate monophosphate (cdGMP), an agonist of the stimulator of interferon genes (STING) pathway, and monophosphoryl lipid A (MPLA), an agonist of the Toll-like receptor 4 (TLR4) pathway. STING agonists have gained significant attention in recent years, and MPLA was clinically approved for use as the first molecular vaccine adjuvant in humans. Both cdGMP and MPLA target host pattern recognition receptors (PRRs), which recognize conserved, immunogenic molecules from viruses and bacteria (i.e., specific nucleic acids, cell membrane components) to trigger the appropriate immune response. STING agonists are cyclic dinucleotides and small-molecule second messengers that, when free in the cytosol, bind STING machinery to trigger a robust production of Type I interferons. MPLA, a derivative of lipopolysaccharide (LPS) has been shown to trigger a strong pro-inflammatory Th1 cytokine response. When both agonists were co-loaded into the same nanoparticle, we observed a 10-fold increase of interferon R(IFNβ) production compared to the single-agonist nanoparticle variants. We have shown that the dual-agonist nanoparticle elicited functional synergy producing high levels of IFNβ, which powered antigen-presenting cells (APCs) to mediate an adaptive cytotoxic CD8+ T cell response and activated natural killer (NK) cells. This stems from the fact that the nanoparticle guarantees delivery to APCs in the perivascular area and enables functional synergy by the uptake of both agonists by the same cell. Notably, dormant cancer cells are also hiding in the perivascular niche.

Facilitating Proficient Intracellular Presentation of Each Agonist

Figure 9A:
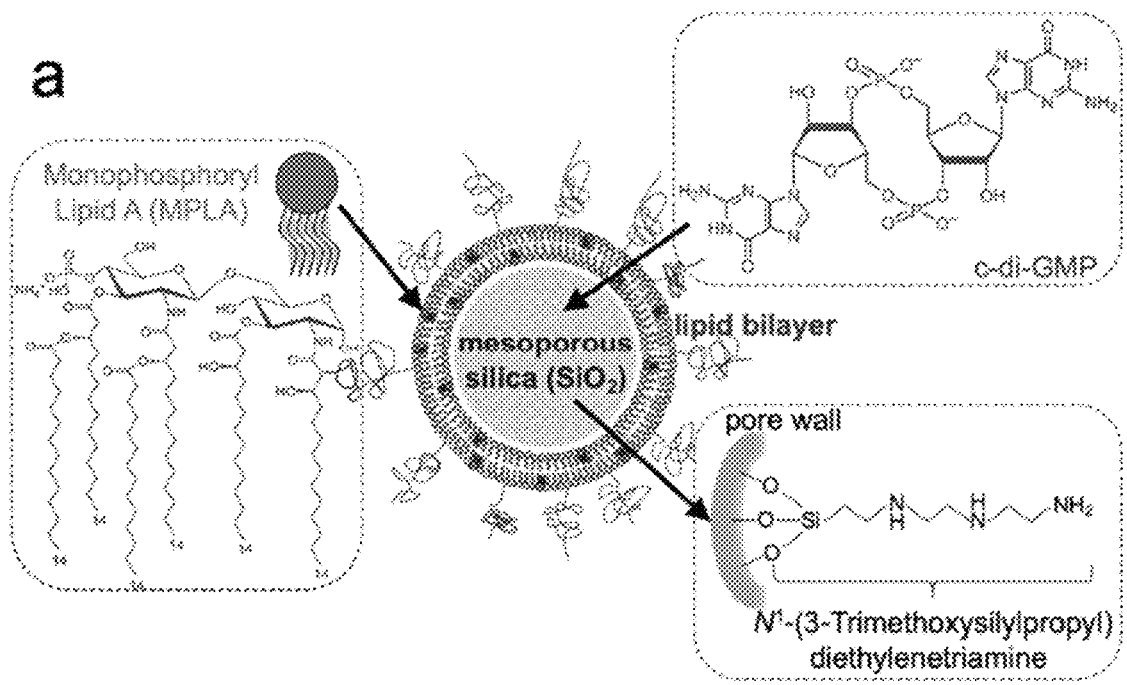
FIGS. 9(A-B) are an illustration of the multicomponent immuno-nanoparticle platform that shows (A) the immuno-nanoparticle construct having a functionalized mesoporous silica nanocore, and an external lipid bilayer component loaded with the dual cargo of MPLA and cdGMP, and (B) the intracellular delivery of each agonist to its specific target.
Figure 9B:
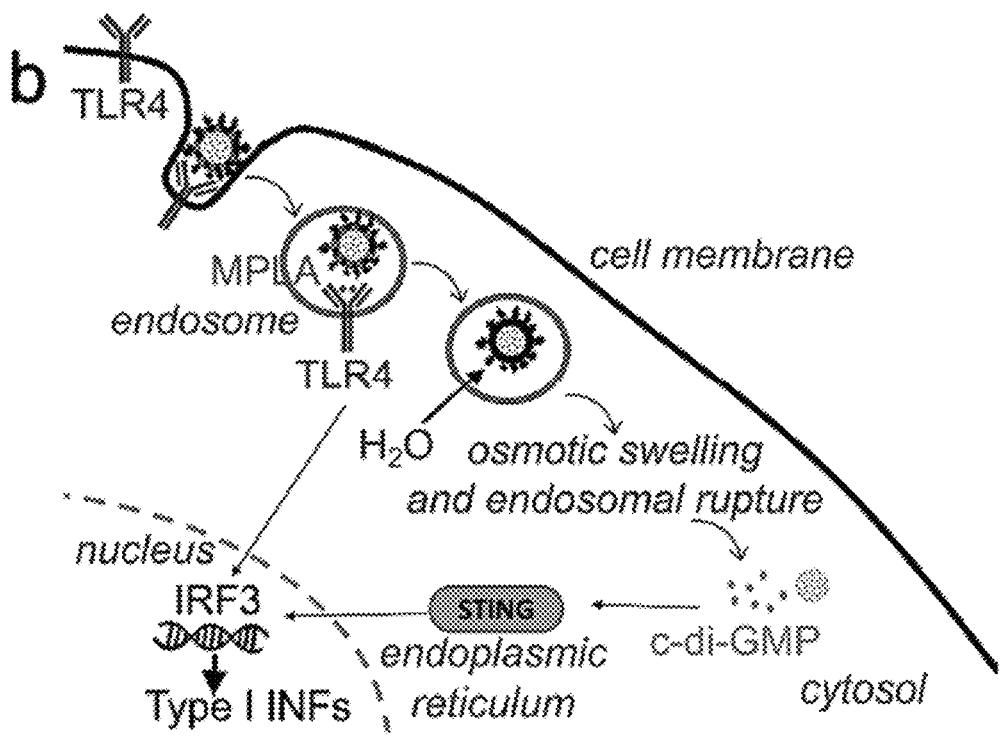

Ideally, the immuno-nanoparticle should protect its cargo from degradation, avoid non-specific distribution throughout the body leading to systemic toxicities, delivery to the disease site and facilitate direct uptake by specific cell subpopulations in the TME (i.e., APCs). Immune-potentiating molecules either in their free unmodified form or in a nanoparticle typically lack one or more of these necessary functions. Further, it is equally important that the immuno-NP effectively presents each immune agonist to the appropriate intracellular location. FIG. 9A illustrates the immuno-NP, which incorporates a multicomponent design with each component having a purposeful function. The external component consists of a lipid bilayer that incorporates the lipophilic MPLA, which is directly presented to the TLR4-expressing cellular and endosomal membrane (FIG. 9B). The internal component consists of a mesoporous silica nanocore, which provide a mechanism for the immuno-NP to escape endosomes, avoid lysosomal degradation and transition to the cytosol via the 'proton sponge' mechanism. To enhance endosomal escape, the mesoporous silica nanocore's surface was functionalized with $N^1$-(3-Trimethoxysilylpropyl)diethylenetriamine. The 'proton sponge' mechanism is based on the high pH buffering capability of the immuno-NP. Functionalization of the huge surface area of the mesoporous silica nanocore with diethylenetriamine provides a very high content of protonatable primary and secondary amine groups with pKa close to endosomal and lysosomal pH. As the endosome matures, the membrane-bound ATPase proton pumps translocate protons from the cytosol into the endosomes to cause acidification and activation of hydrolytic enzymes. However, the 'proton sponge' becomes protonated and opposes the endosome's acidification. In an attempt to achieve acidification, more protons are continuously pumped into the endosome, which is followed by passive entry of chloride ions, leading to water influx. As a result, osmotic swelling and rupture of the endosome causes it to release its contents (nanoparticles) into the cytosol. At the same time, the lower pH being below the pKa of cdGMP causes protonation of its phosphate groups, which eliminates the electrostatic interactions with the silica's surface resulting in efficient release of the STING agonist from the particle into the cytosol.

Orchestrating Systemic Delivery to the APC-Rich Perivascular Regions of the Metastatic TME We have shown that passive deposition of untargeted nanoparticles occurs primarily in the near-perivascular regions of early metastasis which coincides with the APC-rich tumor areas resulting in uptake by the desirable subset of cells in the TME. Here we seek to further increase the selectivity of the immuno-NP for these areas. Perivascular overexpression of fibronectin in the extracellular of mTNBC matrix is a highly targetable biomarker. This is a desirable target as it directs the immuno-NP in the APC-rich perivascular region of metastatic TNBC. We have shown that systemic administration of the immuno-NP resulted in significant deposition in sites of metastasis, predominantly in APC-rich perivascular regions. The site-specific cytokine gradient driven largely by IFNβ resulted in APC- and NK cell-driven immune recruitment from both local and systemic immunity to the tumor site driving the activity of CD8+ T cells. Since safety considerations are paramount for systemically administered immunotherapies, we performed blood and hepatoxicity tests over the period of a month. Any immuno-NP-mediated toxicity was minimal and transient, with recovery observed within just 4-7 days.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. An immuno-nanoparticle construct for systemic administration comprising:
   a nanoparticle carrier;
   a (STING) pathway agonist; and
   a (TLR4) agonist, wherein the STING pathway agonist and the TLR4 agonists are co-loaded into the nanoparticle carrier.

2. The construct of claim 1, the nanoparticle carrier comprising a lipid-based nanoparticle carrier.

3. The construct of claim 1, the lipid-based nanoparticle carrier selected from the group consisting of a liposome, a solid lipid nanoparticle (SLN), and a nanostructured lipid carrier (NLC).

4. The construct of claim 3, the lipid-based nanoparticle carrier comprising a liposome.

5. The construct of claim 1, the nanoparticle carrier comprising a mesoporous silica nanocore and an external lipid bilayer coated around the nanocore, wherein the STING pathway agonist is encapsulated within the nanocore and the TLR4 agonist is incorporated in the lipid bilayer.

6. The construct of claim 1, wherein the mesoporous silica nanocore surface is functionalized with $N^1$-(3-Trimethoxysilylpropyl)diethylenetriamine.

7. The construct of claim 1, the TLR4 agonist comprising a lipopolysaccharide (LPS) derivative or analog thereof.

8. The construct of claim 7, the TLR4 agonist comprising a lipid A analog, variant, derivative, or mimetic.

9. The construct of claim 7, the TLR4 agonist comprising monophosphoryl lipid A (MPLA).

10. The construct of claim 1, the STING pathway agonist comprising a cyclic dinucleotide (CDN).

11. The construct of claim 10, the CDN selected from the group consisting of cyclic dimeric guanosine monophosphate (cdGMP), cyclic dimeric adenosine monophosphate (cdAMP), and cyclic GMP-AMP (cGAMP).

12. The construct of claim 11, the CDN comprising cyclic diguanylate monophosphate (cdGMP).

13. The construct of claim 1, further comprising at least one targeting moiety.

14. The construct of claim 13, wherein the at least one targeting moiety is linked to the exterior surface of the lipid nanoparticle carrier.

15. A method of treating cancer in a subject, the method comprising:
   administering systemically to the subject a therapeutically effective amount of an immuno-nanoparticle construct, the construct including a nanoparticle carrier, a STING pathway agonist, and a TLR4 agonist, wherein the STING pathway agonist and the TLR4 agonist are co-loaded in the nanoparticle carrier, and wherein the STING pathway agonist and the TLR4 agonist synergize to generate a greater amount of Type 1 interferon β in the subject compared to administration of either agent alone.

16. The method of claim 15, the nanoparticle carrier comprising a lipid-based nanoparticle carrier.

17. The method of claim 15, the lipid-based nanoparticle carrier selected from the group consisting of a liposome, a solid lipid nanoparticle (SLN), and a nanostructured lipid carrier (NLC).

18. The method of claim 17, the lipid-based nanoparticle carrier comprising a liposome.

19. The method of claim 15, the nanoparticle carrier comprising a mesoporous silica nanocore and an external lipid bilayer coated around the nanocore, wherein the STING pathway agonist is encapsulated within the nanocore and the TLR4 agonist is incorporated in the lipid bilayer.

20. The method of claim 15, wherein the mesoporous silica nanocore surface is functionalized with $N^1$-(3-Trimethoxysilylpropyl)diethylenetriamine.

21. The method of claim 15, the TLR4 agonist comprising monophosphoryl lipid A (MPLA) and the STING pathway agonist comprising cyclic diguanylate monophosphate (cdGMP).

22. The method of claim 15, wherein the therapeutically effective amount is the amount effective to promote antigen presenting cell (APC) and natural killer (NK) cell driven anti-tumor response in the subject and to inhibit tumor microenvironment (TME) immunosuppression in the subject.

23. The method of claim 15, wherein the immuno-nanoparticle construct is administered intravenously.

24. The method of claim 15, wherein the cancer is selected from breast and melanoma cancer.

25. The method of claim 24, wherein the cancer is metastatic triple negative breast cancer.

26. An immuno-nanoparticle construct for systemic administration comprising:
   a nanoparticle carrier, wherein the nanoparticle carrier includes a mesoporous silica nanocore and an external lipid bilayer coated around the nanocore;
   a (STING) pathway agonist; and
   a (TLR4) agonist, wherein the STING pathway agonist is encapsulated within the nanocore of the nanoparticle carrier and wherein the TLR4 agonist is incorporated within the lipid bilayer of the nanoparticle carrier.

27. The method immuno-nanoparticle construct of claim 26, the TLR4 agonist comprising monophosphoryl lipid A (MPLA) and the STING pathway agonist comprising cyclic diguanylate monophosphate (cdGMP).

* * * * *